(12) United States Patent
Nishigaki et al.

(10) Patent No.: US 7,087,744 B2
(45) Date of Patent: Aug. 8, 2006

(54) FLUORESCENT NUCLEOTIDES AND LABELING METHODS USING THE SAME

(75) Inventors: Junji Nishigaki, Kanagawa (JP); Kouki Nakamura, Kanagawa (JP); Kazuya Takeuchi, Kanagawa (JP); Hiroko Inomata, Saitama (JP); Masayoshi Kojima, Saitama (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 439 days.

(21) Appl. No.: 10/196,223

(22) Filed: Jul. 17, 2002

(65) Prior Publication Data

US 2003/0113755 A1  Jun. 19, 2003

(30) Foreign Application Priority Data

Jul. 19, 2001 (JP) .............................. 2001-219211

(51) Int. Cl.
*C07H 21/00* (2006.01)
*C07H 21/02* (2006.01)
*C07H 21/04* (2006.01)
*C12Q 1/68* (2006.01)
*C12P 19/34* (2006.01)

(52) U.S. Cl. .................... 536/26.6; 536/23.1; 536/25.3; 435/6; 435/91.1

(58) Field of Classification Search ................ 536/23.1, 536/25.3, 26.6; 435/6, 91.1
See application file for complete search history.

(56) References Cited

U.S. PATENT DOCUMENTS

| | | | |
|---|---|---|---|
| 5,476,928 | A | 12/1995 | Ward et al. |
| 5,569,587 | A | 10/1996 | Waggoner |
| 2002/0064794 | A1* | 5/2002 | Leung et al. .................. 435/6 |

FOREIGN PATENT DOCUMENTS

| | | | |
|---|---|---|---|
| GB | 870753 | | 6/1961 |
| JP | 2-191674 | | 7/1990 |
| JP | 3-146565 | * | 6/1991 |

* cited by examiner

*Primary Examiner*—Jezia Riley
(74) *Attorney, Agent, or Firm*—Sughrue Mion, PLLC

(57) ABSTRACT

Fluorescent nucleotides useful for labeling nucleic acids which are represented by the formula: X—Y—Z wherein X represents a residue of natural or non-natural nucleotide and the like and binds to Y at a basic moiety of the residue; Y represents a divalent bridging group or a single bond; Z represents a monovalent group derived from a compound represented by the formula (I) wherein $R^1$ to $R^4$ represent an alkyl group; $V^1$ to $V^6$ represent a hydrogen atom or a substituent; $L^1$ to $L^7$ represent a methine group; W represents an oxygen atom, a sulfur atom, —$C(R^3)(R^4)$— or —$N(R^5)$— wherein $R^3$ to $R^5$ represents an alkyl group; Q represents a nitrogen atom or —$C(V^7)$— wherein $V^7$ represents a hydrogen atom or a monovalent substituent; M represents a counter ion; m represents a number required to neutralize the charge of the molecule; s, t and u represent 0 or 1 or the like, and binds to Y at a reactive group existing in $R^1$ or $R^2$

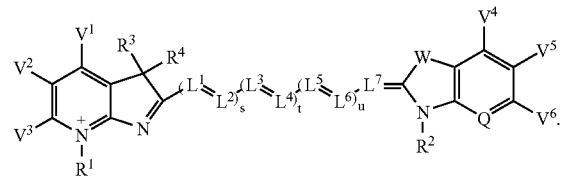

$(M)_m$

15 Claims, No Drawings

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: PCR primer 1

```
-continued
<400> SEQUENCE: 1
tggccgcctt caacgctcag                                                20

<210> SEQ ID NO 2
<211> LENGTH: 26
<212> TYPE: DNA
<213> ORGANISM: Artificial Sequence
<220> FEATURE:
<223> OTHER INFORMATION: PCR primer 2

<400> SEQUENCE: 2
tcaggcactt tcattaacag gcacat                                         26
```

FLUORESCENT NUCLEOTIDES AND LABELING METHODS USING THE SAME

FIELD OF THE INVENTION

The present invention relates to azamethine compounds useful as fluorescence-labeling reagents, fluorescent nucleotides including the same and utilization of the same.

RELATED ART

One of molecular-biological methods most widely used for detecting a homologous nucleic acid sequence is formation of a hybrid of DNA/DNA, RNA/RNA, or RNA/DNA. In this method, a nucleic acid (DNA or RNA) used as a probe is labeled, and the labeled nucleic acid is hybridized with a nucleic acid to be detected (DNA or RNA). When a homology exists between the nucleic acid used as a probe and the nucleic acid to be detected, single-stranded nucleic acids complementary to each other hybridize to form a double strand, and the double strand is detected by utilizing the label of the probe.

When a nucleic acid is used as a probe, methods comprising the step of labeling the probe with a radioisotope have conventionally been used, and presence or absence of hybridization of the probe and a target nucleic acid is detected by autoradiography. The methods utilizing a radioisotope to label a gene probe are particularly excellent in high sensitivity, but are troublesome because of problems associated with handling of a radioisotope such as ensuring of laboratory safety and disposal of waste radioactive compounds. Further, they also suffer from a problem that a radioisotope has a half life and can be used only for a certain period of time.

For the above reasons, non-radioactive labeling methods have been developed as simpler methods. For example, methods are known which comprise the step of labeling a gene probe with a biotin molecule (European Patent No. 63879) or digoxigenin molecule (European Patent Publication No. 324474A1). After the labeled nucleic acid probe and a nucleic acid sequence to be detected are hybridized, the biotin molecule or digoxigenin molecule exists in the formed double-stranded nucleic acid. After the hybridization, a nucleic acid hybridized with the probe can be detected by binding a (strept)avidin-marker enzyme complex or anti-digoxigenin antibody-marker enzyme complex for digoxigenin to these molecules. However, such detection methods using an enzyme are not sufficient in sensitivity or specificity.

Further, besides the aforementioned methods, various methods comprising the step of labeling a target substance with a fluorescent dye have been studied. Performances required for the fluorescence-labeling reagent include (1) the agent has a high fluorescence quantum yield, (2) the agent has a high molar extinction coefficient, (3) the agent is water-soluble and free from aggregate in an aqueous solvent to cause self-quenching, (4) the agent is hardly hydrolyzed, (5) the agent is hardly suffered from photodegradation, (6) the agent is hardly influenced by background fluorescence, (7) the agent is introduced with a reactive substituent that produces a covalent bond with a target substance and the like. Fluorescein isothiocyanate (FITC) and rhodamine isothiocyanate, which have been known as fluorescence-labeling reagents since old time, have a high fluorescence quantum yield. However, they are susceptible to influence by, for example, background fluorescence of a membrane used for blotting, because their molar extinction coefficient are low and their excitation and emission wavelengths are within the range of 500 nm to 600 nm.

As dyes having a high molar extinction coefficient, for example, cyanine dyes disclosed in U.S. Pat. No. 5,486,616, Japanese Patent Unexamined Publication (Kokai) Nos. 2-191674, 5-287209, 5-287266, 8-47400, 9-127115, 7-145148 and 6-222059, and polymethine dyes such as oxonol barbiturate disclosed in Journal of Fluorescence, 5, p.231 (1995) are known. However, these dyes have problems that they are hardly soluble in water, they are hydrolyzed even if they are dissolved in water and the like. In addition, they often form aggregates in an aqueous medium due to their strong interaction among dye molecules, which results in observation of self-quenching of fluorescence. The cyanine dyes disclosed in Japanese Patent Unexamined Publication (Kokai) No.2-191674 and the like are superior dyes that are imparted with water-solubility and suppressed formation of aggregates by introduction of a sulfonate group into a relatively stable chromophore. However, their fluorescence quantum yield are not satisfactory high, and they also have a problem that syntheses of the dyes are difficult due to the introduced sulfonate group. Under such circumstances, development of a fluorescent dye has been desired which has characteristics of high water-solubility and stability to prevent self-quenching due to aggregation, as well as strong fluorescence.

An example of dyes having another dye backbone structure with strong fluorescence includes azaindolenine cyanine dyes disclosed in British Patent No. 870,753. However, the patent document fails to disclose characteristics essential for fluorescence-labeling reagents such as water-solubility, aggregation property, stability of aqueous solutions and the like. Furthermore, the document discloses no example of introduction of a reactive substituent that can produce a covalent bond with a target substance. Therefore, competence of the azaindolenine cyanine dyes as fluorescence-labeling reagents has not yet been clarified. Further, Japanese Patent Unexamined Publication (Kokai) Nos. 4-358143, 3-135553, 1-280750 and European Patent No. 341958 disclose examples of applications of the azaindolenine cyanines for photographic purpose. However, these applications are based on utilization of absorption characteristics of the azaindolenine cyanines, and do not focus their luminescence characteristics for positive utilization thereof.

SUMMARY OF THE INVENTION

An object of the present invention is to provide a novel fluorescent nucleotide useful for labeling a nucleic acid and, more specifically, a fluorescent nucleotide that can avoid the aforementioned problems of the conventional techniques. The inventors of the present invention conducted various studies to achieve the aforementioned object. As a result, they found that, when a complex of a nucleotide was formed by using an azamethine compound recently developed as a fluorescence-labeling reagent and a nucleic acid, and a nucleic acid was labeled and detected by using said complex, superior uptake rate of the complex into the nucleic acid and superior fluorescence intensity upon detection were obtained, and thus achieved the present invention.

The present invention thus provides fluorescent nucleotides represented by the formula: X—Y—Z

[in the formula, X represents a residue of a natural or non-natural nucleotide, an oligonucleotide, a polynucleotide, or a derivative thereof which binds to Y at a basic moiety of said residue; Y represents a divalent bridging group or a single bond; Z represents a monovalent group derived from a compound represented by the following general formula (I):

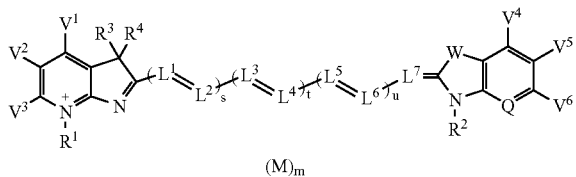

(in the formula, $R^1$, $R^2$, $R^3$, and $R^4$ independently represent a substituted or unsubstituted alkyl group, $R^3$ and $R^4$ may bind to each other to form a saturated or unsaturated ring; $V^1$, $V^2$, $V^3$, $V^4$, $V^5$, and $V^6$ represents a hydrogen atom or a substituent, $V^1$ and $V^2$, $V^2$ and $V^3$, $V^4$ and $V^5$, and/or $V^5$ and $V^6$ may bind to each other to form a saturated or unsaturated ring; $L^1$, $L^2$, $L^3$, $L^4$, $L^5$, $L^6$ and $L^7$ independently represent a substituted or unsubstituted methine group; W represents an oxygen atom, a sulfur atom, —C($R^3$)($R^4$)— or —N($R^5$)— ($R^3$, $R^4$, and $R^5$ independently represent a substituted or unsubstituted alkyl group); Q represents a nitrogen atom or —C($V^7$)— ($V^7$ represents a hydrogen atom or a monovalent substituent and may bind to $V^6$ to form a saturated or unsaturated ring); M represents a counter ion; m represents a number required to neutralize the charge of the molecule; s represents 0 or 1; t represents 0 or 1; and u represents 0 or 1);

a compound represented by the following general formula (II):

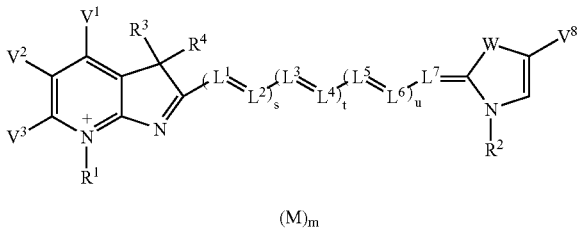

(in the formula, $V^1$, $V^2$, $V^3$, $R^1$, $R^2$, $R^3$, $R^4$, $L^1$, $L^2$, $L^3$, $L^4$, $L^5$, $L^6$, $L^7$, W, M, m, s, t, and u have the same meanings as defined above; $V^8$ represents a hydrogen atom or a monovalent substituent, provided that, when W represents —N($R^5$)— or —C($R^3$)($R^4$)—, $V^8$ may bind to a substituent on W to form a saturated or unsaturated ring); or a compound represented by the following general formula (III):

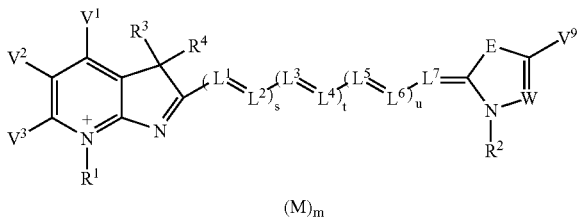

(in the formula, $V^1$, $V^2$, $V^3$, $R^1$, $R^2$, $R^3$, $R^4$, $L^1$, $L^2$, $L^3$, $L^4$, $L^5$, $L^6$, $L^7$, W, M, m, s, t, and u have the same meanings as defined above; E represents a nitrogen atom or —C($R^6$)═ ($R^6$ represents a hydrogen atom or a monovalent substituent); $V^9$ represents a hydrogen atom or a monovalent substituent and $V^9$ may bind to $R^6$ to form a saturated or unsaturated ring), and Z binds to Y at a reactive group existing in $R^1$ or $R^2$].

According to preferred embodiments of the present invention, there are provided the aforementioned fluorescent nucleotides, wherein at least one of $R^1$ and $R^2$ is an alkyl group substituted with an active ester group (said active ester group can covalently bond to an amino group, a hydroxyl group, or a thiol group) in Y; the aforementioned fluorescent nucleotides, wherein at least one of $R^1$ and $R^2$ is an alkyl group substituted with a carboxyl group in Y; and the aforementioned fluorescent nucleotides, wherein X is a residue of a nucleotide or a derivative thereof.

According to more preferred embodiments, there are provided the aforementioned fluorescent nucleotides, wherein X is a residue of a nucleotide or a derivative thereof selected from the group consisting of:

(1) a nucleotide selected from the group consisting of AMP, ADP, ATP, GMP, GDP, GTP, CMP, CDP, CTP, UMP, UDP, UTP, TMP, TDP, TTP, 2-Me-AMP, 2-Me-ADP, 2-Me-ATP, 1-Me-GMP, 1-Me-GDP, 1-Me-GTP, 5-Me-CMP, 5-Me-CDP, 5-Me-CTP, 5-MeO-CMP, 5-MeO-CDP, and 5-MeO-CTP (Me represents a methyl group, MeO represents a methoxy group, and a numeral before Me or MeO represents a substituting position), (2) a nucleotide selected from the group consisting of deoxynucleotides and dideoxynucleotides corresponding to the nucleotides mentioned in (1); and (3) a nucleotide derivative derived from the nucleotides mentioned in (1) and (2); the aforementioned fluorescent nucleotides, wherein Y represents -$CH_2$—, —CH═CH—, —C═C—, —CO—, —O—, —S—, —NH—, or a bridging group consisting of a combination thereof (a hydrogen atom on the bridging group may be replaced with other substituent); and the aforementioned fluorescent nucleotides, wherein Y represents an aminoallyl group.

From another aspect, the present invention provides a method for producing a fluorescence-labeled nucleic acid comprising a step of performing a nucleic acid synthesis reaction by using a nucleic acid synthetase, a template nucleic acid, and any of the aforementioned fluorescent nucleotides. According to a preferred embodiment of this method, there is provided the aforementioned method, wherein the nucleic acid synthesis reaction comprises one or more reactions selected from the group consisting of a reverse transcription reaction, terminal transferase reaction, reactions of random prime method, PCR, and nick translation.

From yet anther aspect, there are provided nucleic acid probes or primers labeled with any of the aforementioned fluorescent nucleotides; reagents for detecting a nucleic acid comprising any of the aforementioned nucleic acid probes or primers; the aforementioned reagents for detecting a nucleic acid for use in diagnosis of a disease; and kits for detecting a nucleic acid, which comprises (1) any of the aforementioned fluorescent nucleotides, (2) nucleic acid synthetase, and (3) a buffer.

The present invention also provides the aforementioned azamethine dyes represented by the general formula (I) (preferably the aforementioned azamethine dyes, wherein W represents —C($R^3$)($R^4$)— or an oxygen atom, and the aforementioned azamethine dyes, wherein W represents —C($R^3$)($R^4$)— and Y represents a nitrogen atom); the aforementioned azamethine dyes represented by the general formula (II) (preferably the aforementioned azamethine dyes, wherein W represents —C($R^3$)($R^4$)— or a sulfur atom); and the aforementioned azamethine dyes represented by the general formula (III) (preferably the aforementioned azamethine dye, wherein W represents an oxygen atom). Further, there are also provided the aforementioned azamethine dyes represented by the general formula (I), (II), or (III), wherein at least one of $R^1$ and $R^2$ represents an alkyl group substituted with a reactive group that can covalently bind to a compound to be labeled; the aforementioned azamethine dyes represented by the general formula (I), (II), or (III), wherein at least one of $R^1$ and $R^2$ represents an alkyl group substituted with an active ester group (said active ester group can covalently bind to an amino group, a hydroxyl group, or a thiol group in a compound to be labeled); and the aforementioned azamethine dyes represented by the general formula (I), (II), or (III), wherein at least one of $R^1$ and $R^2$ represents an alkyl group substituted with a carboxyl group.

The present invention further provides use of the aforementioned compounds represented by the general formula (I), (II), or (III) for preparation of the aforementioned fluorescent nucleotides; use of the aforementioned compounds represented by the general formula (I), (II), or (III) for preparation of the aforementioned nucleic acid probes or primers; use of the aforementioned compounds represented by the general formula (I), (II), or (III) for preparation of the aforementioned reagents for detecting a nucleic acid; and methods for diagnosing a disease which comprises the step of bringing the aforementioned reagent for detecting a nucleic acid into contact with a biological sample collected from a mammal including human.

BEST MODE FOR CARRYING OUT THE INVENTION

Examples of the natural or non-natural nucleotide represented by X include, for example, (1) nucleotides of AMP, ADP, ATP, GMP, GDP, GTP, CMP, CDP, CTP, UMP, UDP, UTP, TMP, TDP, TTP, 2-Me-AMP, 2-Me-ADP, 2-Me-ATP, 1-Me-GMP, 1-Me-GDP, 1-Me-GTP, 5-Me-CMP, 5-Me-CDP, 5-Me-CTP, 5-MeO-CMP, 5-MeO-CDP, and 5-MeO-CTP (Me represents a methyl group, MeO represents a methoxy group, and a numeral before Me or MeO represents a substituting position), (2) deoxynucleotides corresponding to the aforementioned nucleotides and dideoxynucleotides corresponding to the aforementioned nucleotides, and (3) derivatives further derived from the nucleotides mentioned in (1) and (2) and the like. However, the nucleotides are not limited to these examples. Specific examples of the natural or non-natural nucleotide include, but not limited thereto, ATP, CTP, GTP, TTP, UTP, dATP, dCTP, dGTP, dTTP, dUTP, ddATP, ddCTP, ddGTP, ddTTP, ddUTP, derivatives thereof and the like.

Examples of the oligonucleotide include oligonucleotides obtained by polymerizing abut 1 to 50, preferably about 1 to 30, more preferably about 1 to 20, of the aforementioned nucleotides or derivatives thereof, and each of constitutional unit nucleotides may be the same or different. The polynucleotide is a polymer obtained by polymerizing a large number of the aforementioned nucleotides or derivatives thereof, and its size (length) is not particularly limited. For example, the size may be several bp to several kb as the number of bases. The term "fluorescent nucleotide" used in the specification encompasses any compounds whose nucleic acid moiety is the aforementioned nucleotides, oligonucleotides, and polynucleotides as described above, and should be construed in the broadest sense.

X binds to Y at a base moiety of a residue of the nucleotide. Examples of the base moiety of the nucleotide residue include purine derivatives and pyrimidine derivatives. A position of the purine base that forms a bond with the bridging group Y is not particularly limited so long as the position is other than the 9th position which forms a bond with a saccharide component. For example, when the purine base is adenine, X can bind to the bridging group Y at the 2nd or 8th position, or via an amino group existing at the 6th position. When the purine base is guanine, X can bind to the bridging group Y at the 1st or 8th position or via an amino group existing at the 2nd position. The binding position for the bridging group Y in the pyrimidine base is not particularly limited so long as the position is other than the 1st position which forms a bond with a saccharide component. For example, when the pyrimidine base is cytosine, X can bind to the bridging group Y at the 5th or 6th position or via an amino group existing at the 4th position. When the pyrimidine base is thymine, X can bind to the bridging group Y at the 3rd or 6th position or via a methyl group existing at the 5th position. Furthermore, when the pyrimidine base is uracil, X can bind to the bridging group Y at the 3rd, 5th, or 6th position.

In the aforementioned formula, Y represents a divalent bridging group or a single bond. Type of the bridging group is not particularly limited so long that characteristics of the fluorescent nucleotides of the present invention, such as stability as a fluorescent nucleotide compound, water-solubility, uptake rate into a nucleic acid, and fluorescence intensity, are not significantly influenced. Those skilled in the art can appropriately chose a divalent bridging group suitable for binding a nucleotide moiety represented by X with a fluorescent compound moiety represented by Z. Examples of the bridging group Y include —$CH_2$—, —CH=CH—, —C≡C—, —CO—, —O—, —S—, —NH— and bridging groups composed of a combination thereof, and one or more hydrogen atoms on the bridging group may be replaced with other substituents. The number of carbon atoms in the backbone of the bridging group is not particularly limited, and is generally 1 to 50, preferably 1 to 20, more preferably 1 to 10, and most preferably about 1 to 5.

Z represents a monovalent group derived from any of the azamethine dyes represented by the general formula (I), (II), or (III) and binds to Y at a reactive group existing in $R^1$ or $R^2$.

In the general formulas (I), (II), and (III), $R^1$ and $R^2$ may be the same or different and preferably represent an alkyl group having 1 to 20 carbon atoms. The alkyl group may be a straight, branched, cyclic alkyl, or a combination thereof (in the specification, other alkyl groups or an alkyl moiety in other substituents having the alkyl moiety have the same meaning). For example, examples include methyl group, ethyl group, n-propyl group, butyl group, cyclohexyl group and the like. The aforementioned alkyl group may have one or more substituents at any positions. The substituents on the alkyl group are not particularly limited. Preferably, a reactive substituent is introduced for labeling a substance comprising an antibody, protein, peptide, enzyme substrate, hormone, lymphokine, metabolite, receptor, antigen, hapten, lectin, avidin, streptavidin, toxin, carbohydrate, polysaccharide, nucleic acid, deoxynucleic acid, derived nucleic acid, derived deoxynucleic acid, DNA fragment, RNA fragment, derived DNA fragment, derived RNA fragment, natural drug, virus particle, bacterial particle, virus component, yeast component, blood cell, blood cell component, bacterium, bacterial component, natural or synthetic lipid, synthetic chemical, poison, environmental pollutant, polymer, polymer particle, glass particle, plastic particle, polymer film or the like with a dye through a covalent bond, ionic bond, hydrogen bond or the like.

Type of the reactive substituent is not particularly limited. Examples thereof include a succinimidyl ester group, a halogen-substituted triazinyl group, a halogen-substituted pyrimidinyl group, a sulfonyl halide group, an a-haloacetyl group, maleimidyl group, aziridinyl group and the like. Examples of other substituents include a halogen atom (e.g., fluorine, chlorine, bromine or iodine), a mercapto group, a cyano group, a nitro group, a carboxyl group, a phosphoric acid group, a sulfo group, a hydroxy group, an amino group, an isothiocyanate group, an isocyanate group, an alkoxy group having about 1 to 8 carbon atoms (e.g., methoxy group, ethoxy group and the like), an aryloxy group having about 6 to 20 carbon atoms (e.g., phenoxy group, naphthoxy group and the like), an alkoxycarbonyl group having about 2 to 10 carbon atoms (e.g., methoxycarbonyl group, ethoxycarbonyl group and the like), an aryloxycarbonyl group having about 6 to 20 carbon atoms (e.g., phenoxycarbonyl group and the like), an acyl group having about 2 to 10 carbon atoms (e.g., acetyl group, pivaloyl group and the like), an acyloxy group having about 2 to 8 carbon atoms (e.g., acetyloxy group, benzoyloxy group and the like), an acylamino group having about 2 to 8 carbon atoms (e.g., acetylamino group and the like), a sulfonyl group having about 1 to 8 carbon atoms (e.g., methanesulfonyl group, ethanesulfonyl group, benzenesulfonyl group and the like), a sulfinyl group having about 1 to 20 carbon atoms (e.g., methanesulfinyl group, ethanesulfinyl group, benzenesulfinyl group and the like), a sulfonylamino group having about 1 to 8 carbon atoms (e.g., methanesulfonylamino group, ethanesulfonylamino group, benzenesulfonylamino group and the like), a carbamoyl group having about 1 to 10 carbon atoms (e.g., carbamoyl group, methylcarbamoyl group, morpholinocarbamoyl group and the like), a substituted amino group having about 1 to 20 carbon atoms (e.g., methylamino group, dimethylamino group, benzylamino group, anilino group, diphenylamino group and the like), a sulfamoyl group having about 2 to 10 carbon atoms (e.g., methylsulfamoyl group, ethylsulfamoyl group, piperidinosulfamoyl group and the like), an ammonium group having about 0 to 15 carbon atoms (e.g., trimethylammonium group, triethylammonium group and the like), a hydrazino group having about 0 to 15 carbon atoms (e.g., trimethylhydrazino group and the like), a ureido group having about 1 to 15 carbon atoms (e.g., ureido group, N,N-dimethylureido group and the like), an imido group having about 1 to 15 carbon atoms (e.g., succinimido group), an alkylthio group having about 1 to 20 carbon atoms (e.g., methylthio group, ethylthio group and the like), an arylthio group having 6 to 20 carbon atoms (e.g., phenylthio group, p-methylphenylthio group, p-chlorophenylthio group, 2-pyridylthio group, naphthylthio group and the like), a substituted or unsubstituted heterocyclic group having about 1 to 20 carbon atoms (e.g., pyridyl group, 5-methylpyridyl group, thienyl group, furyl group, morpholino group, tetrahydrofuryl group, 2-pyrazyl group and the like), an unsaturated hydrocarbon group having about 2 to 18 carbon atoms (e.g., vinyl group, ethynyl group, 1-cyclohexenyl group, benzylidine group, benzylidene group and the like), an aryl group having about 6 to 20 carbon atoms (e.g., phenyl group, 4-sulfophenyl group, 2,5-disulfophenyl group, 4-carboxyphenyl group, naphthyl group and the like) and an alkyl group having about 1 to 20 carbon atoms (e.g., methyl group, ethyl group, propyl group and the like).

As $R^1$ and $R^2$, an alkyl group having 1 to 10 carbon atoms substituted with a carboxyl group, isothiocyanate group, succinimidyl ester group, sulfonyl halide group, α-haloacetyl group, maleimidyl group, sulfonic acid group or a salt thereof are preferred. More preferred examples include an alkyl group having 1 to 6 carbon atoms substituted with a carboxyl group, isothiocyanate group, succinimidyl ester group, sulfonic acid group or a salt thereof, or an arylalkyl group having 7 to 20 carbon atoms substituted with a sulfo group, carboxyl group, isothiocyanate group, succinimidyl ester group, sulfonyl halide group, a-haloacetyl group, or maleimidyl group.

In the general formulas (I), (II) and (III), $R^3$, $R^4$, $R^5$ and $R^6$ may preferably be an alkyl group having 1 to 20 carbon atoms which may have any of the substituents exemplified for $R^1$ and $R^2$ at any position on the alkyl group. Further, $R^3$ and $R^4$ may bind to each other to form a saturated carbon ring. $R^3$, $R^4$, and $R^5$ preferably represent an alkyl group having 1 to 6 carbon atoms, more preferably an alkyl group having 1 to 3 carbon atoms.

In the general formulas (I), (II), and (III), $V^1$, $V^2$, $V^3$, $V^4$, $V^5$, $V^6$, $V^7$, $V^8$, and $V^9$ are the same or different and represent a hydrogen atom or a monovalent substituent. The substituent represented by $V^1$, $V^2$, $V^3$, $V^4$, $V^5$, $V^6$, $V^7$, $V^8$, or $V^9$ is not particularly limited. Examples include those exemplified as the substituents on the alkyl group for $R^1$ and $R^2$.

$V^1$ and $V^2$, $V^2$ and $V^3$, $V^4$ and $V^5$, $V^5$ and $V^6$, and/or $V^6$ and $V^7$ may bind to each other to form, for example, a 5-, 6- or 7-membered saturated or unsaturated ring. The aforementioned unsaturated ring may contain one or more hetero atoms such as an oxygen atom, nitrogen atom, or sulfur atom. One or more substituents selected from those exemplified as the substituents on an alkyl group of $R^1$ and $R^2$ (hereinafter, these substituents are referred to as "exemplified substituents") may substitute at any position of the ring formed.

Examples of $V^1$, $V^2$, $V^3$, $V^4$, $V^5$, $V^6$, $V^7$, $V^8$, and $V^9$ include an alkyl group having 1 to 6 carbon atoms (one or more of the exemplified substituents may exist at any positions on the alkyl group), an aryl group having 6 to 20 carbon atoms (one or more of the exemplified substituents may exist at any positions on the aryl group), a halogen atom, a thioalkyl group having 1 to 10 carbon atoms, an alkylsulfone group having 1 to 10 carbon atoms, a phosphonic acid group, a carboxyl group, an alkoxy group having 1 to 10 carbon atoms, a cyano group, a substituted amino group, an isothiocyanate group, an isocyanate group, a succinimidyl ester group, a halogen-substituted triazinyl group, a halogen-substituted pyrimidinyl group, a sulfonyl halide group, an a-haloacetyl group, a maleimidyl group and an aziridinyl group. More preferred examples include a halogen atom, carboxyl group, and phosphonic acid group, as well as an aryl group having 6 to 20 carbon atoms substituted with a halogen atom, carboxyl group, sulfonic acid group, or phosphonic acid group, an alkoxy group having 1 to 10 carbon atoms substituted with a carboxyl group or sulfo group, and an alkylthio group having 1 to 10 carbon atoms substituted with a carboxyl group, sulfonic acid group, or phosphonic acid group.

In the general formulas (I), (II), and (III), $L^1$, $L^2$, $L^3$, $L^4$, $L^5$, $L^6$, and $L^7$ independently represent a substituted or unsubstituted methine group. Examples of the substituent include a substituted or unsubstituted alkyl group having 1 to 15 carbon atoms, preferably 1 to 10 carbon atoms, most preferably 1 to 5 carbon atoms (e.g., methyl group, ethyl group, carboxyethyl group and the like), a substituted or unsubstituted aryl group having 6 to 30 carbon atoms, preferably 6 to 20 carbon atoms, more preferably 6 to 15 carbon atoms (e.g., phenyl group, o-carboxyphenyl group and the like), a substituted or unsubstituted heterocyclic group having 3 to 20 carbon atoms, preferably 4 to 15 carbon atoms, more preferably 6 to 10 carbon atoms (e.g., N,N-dimethylbarbituric acid group and the like), a halogen atom (e.g., chlorine, bromine, iodine, fluorine and the like), an alkoxy group having 1 to 20 carbon atoms, preferably 1 to 15 carbon atoms, more preferably 1 to 10 carbon atoms (e.g., methoxy group, ethoxy group and the like), an amino group having 0 to 20 carbon atoms, preferably 2 to 15 carbon atoms, more preferably 4 to 15 carbon atoms (e.g., methylamino group, dimethylamino group, N-methyl-N-phenylamino group, N-methylpiperazino group and the like), an alkylthio group having 1 to 15 carbon atoms, preferably 1 to 10 carbon atoms, more preferably 1 to 8 carbon atoms (e.g., methylthio group, ethylthio group and the like), an arylthio group having 6 to 20 carbon atoms, preferably 6 to 18 carbon atoms, more preferably 6 to 15 carbon atoms (e.g., phenylthio group, p-methylthio group and the like) and the like. Symbols s, t, and u independently represent 0 or 1. The compounds wherein s is 0 and t and u are 1, or wherein s and t are 0, and u is 1 are preferred.

M represents a counter ion. M may be a cation or an anion. Examples of the cation include an alkali metal ion such as sodium ion, potassium ion, and lithium ion, and an organic ion such as tetraalkylammonium ion and pyridinium ion. The anion may be an inorganic anion or an organic anion, and examples of the anion include a halide anion (e.g., fluoride ion, chloride ion, bromide ion, iodide ion and the like), a substituted arylsulfonate ion (e.g., p-toluenesulfonate ion, p-chlorobenzenesulfonate ion and the like), an aryldisulfonate ion (e.g., 1,3-benzenedisulfonate ion, 1,5-naphthalenedisulfonate ion and the like), an alkylsulfate ion (e.g., methylsulfate ion and the like), sulfate ion, thiocyanate ion, perchlorate ion, tetrafluoroborate ion, picrate ion, acetate ion, trifluoromethanesulfonate ion and the like. Further, M may also be a hydrogen ion. Preferred examples of the cation include an ammonium ion, an alkali metal ion, a halogen anion, and a substituted arylsulfonate ion, and more preferred examples include an alkali metal ion, a halogen anion, and a substituted arylsulfonate ion. Symbol m represents a number required to neutralize charge of the molecule.

In the general formula (I), W preferably represents an oxygen atom, a sulfur atom, or —C($R^3$)($R^4$)—, more preferably an oxygen atom or —C($R^3$)($R^4$)—. In the general formula (II), W preferably represents a sulfur atom or —C($R^3$)($R^4$)—, more preferably —C($R^3$)($R^4$)—. In the general formula (III), W preferably represents an oxygen atom or —C($R^3$)($R^4$)—, more preferably an oxygen atom. In the general formula (III), E represents a nitrogen atom or —C($R^6$)=, and $R^6$ represents a hydrogen atom or a substituent. Examples of the substituent represented by $R^6$ include the aforementioned "exemplified substituents". It is preferred that $R^6$ binds to $V^9$ to form a saturated or unsaturated ring. A more preferred example includes the compounds where a benzoisoxazole ring is formed as shown in the following general formula (IV):

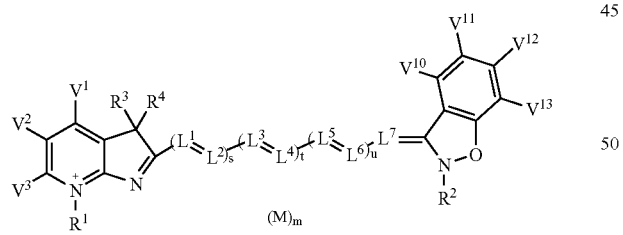

($V^1$, $V^2$, $V^3$, $R^1$, $R^2$, $R^3$, $R^4$, $L^1$, $L^2$, $L^3$, $L^4$, $L^5$, $L^6$, $L^7$, M, m, s, t, and u have the same meanings as those defined above, respectively. Examples of $V^{11}$, $V^{12}$, $V^{13}$ and $V^{14}$, include those exemplified for $V^1$ to $V^9$, and preferred embodiments are also the same as those of $V^1$ to $V^9$.)

The compounds represented by the general formulas (I), (II) and (III) may have one or more asymmetric carbons depending on types of the substituents, and any of stereoisomers such as optical isomers and diastereoisomers, mixtures of stereoisomers, racemates and the like also falls within the scope of the present invention. Further, the compounds represented by the general formulas (I), (II) and (III) may form hydrates or solvates, and any of these substances also falls within the scope of the present invention.

Preferred examples of the compounds represented by the aforementioned general formulas (I), (II) and (III) are shown below. However, the scope of the present invention is not limited to the following specific compounds.

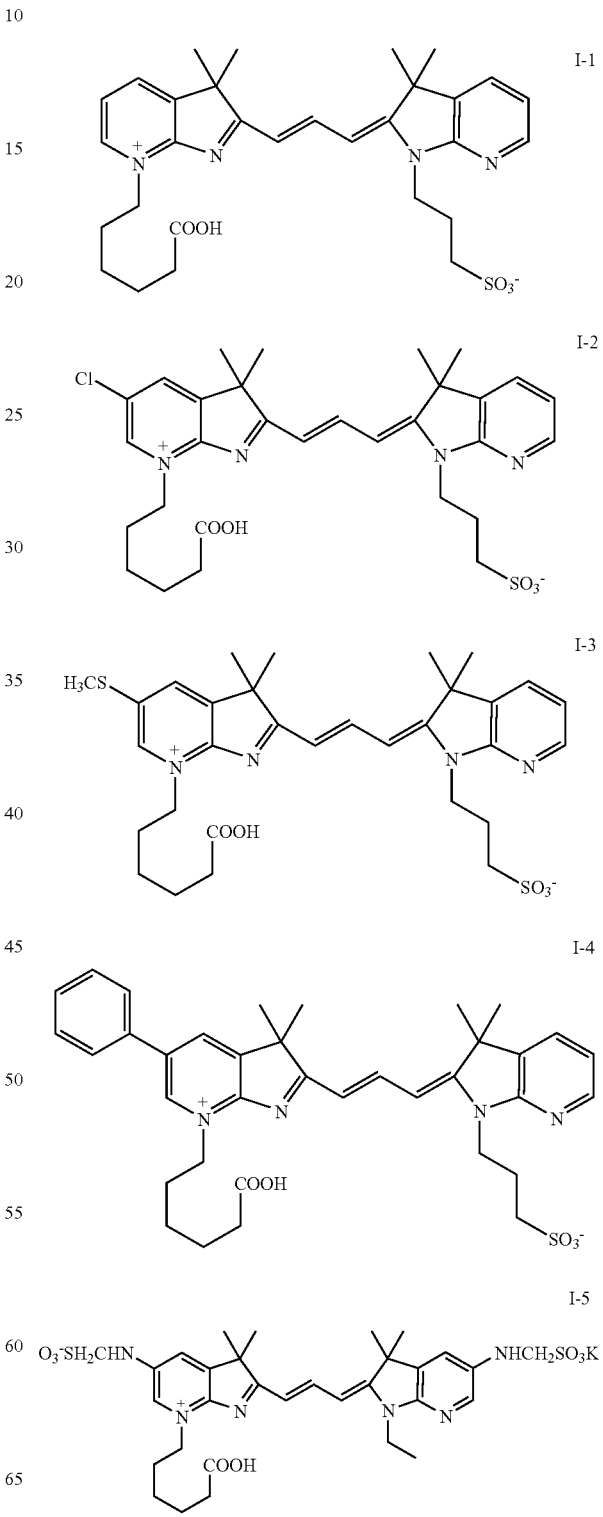

-continued
I-6
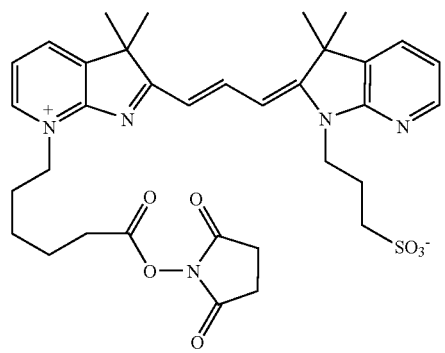
I-7
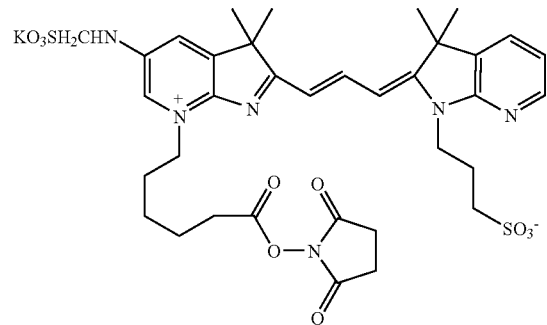
I-8
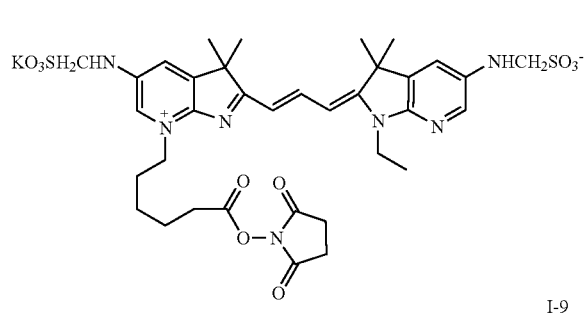
I-9
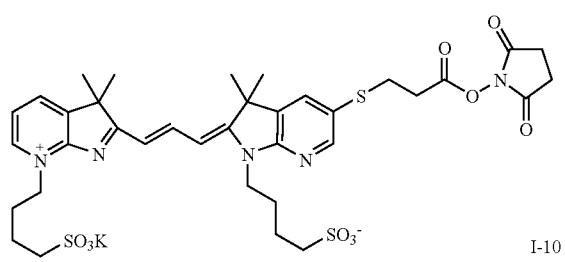
I-10
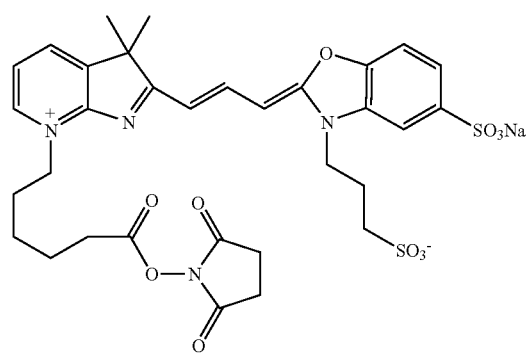
-continued
I-11
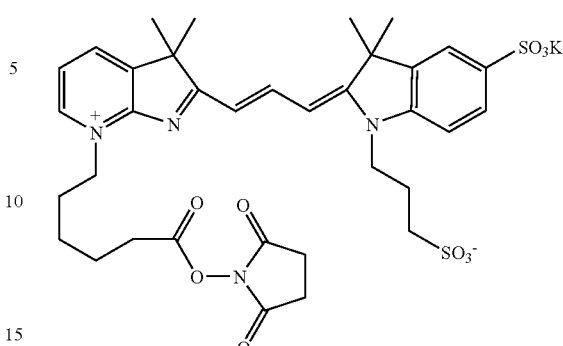
I-12
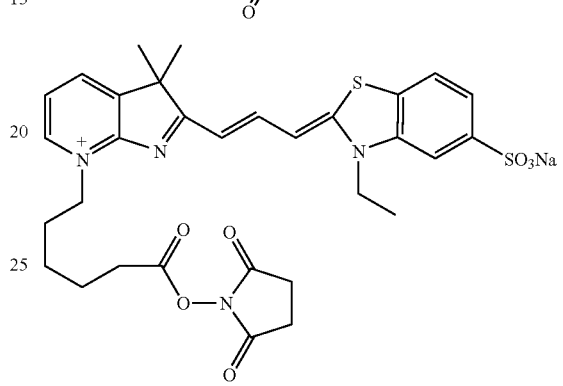
I-13
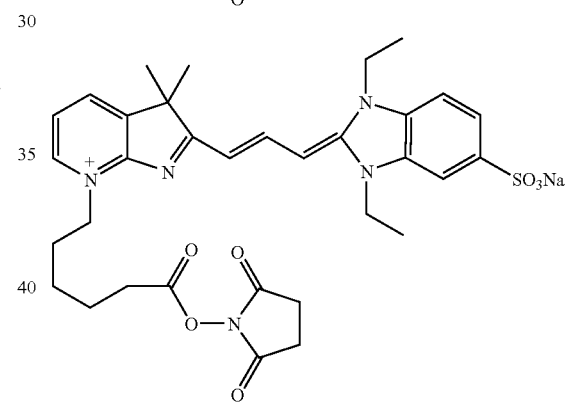
I-14
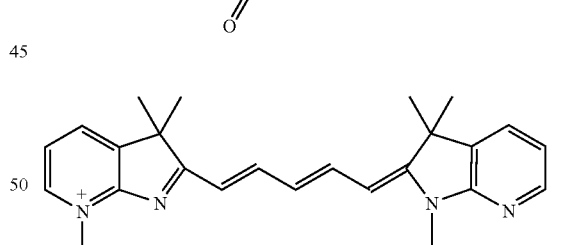
I-15
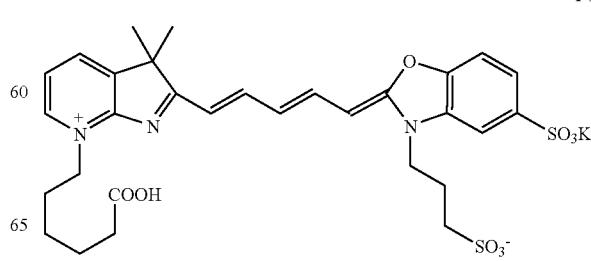

-continued
I-16
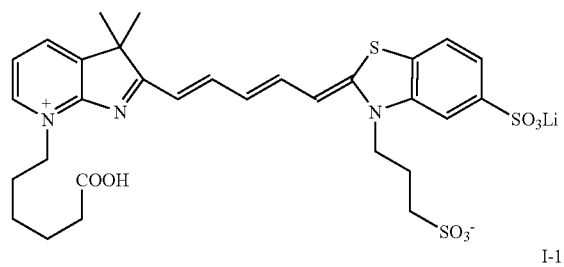
I-17
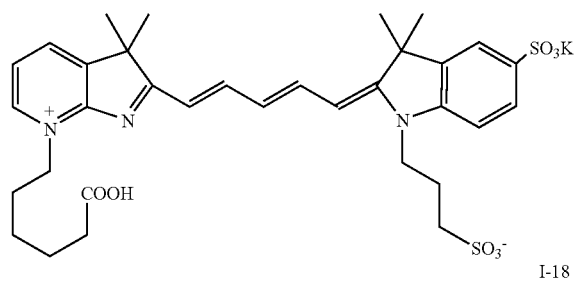
I-18
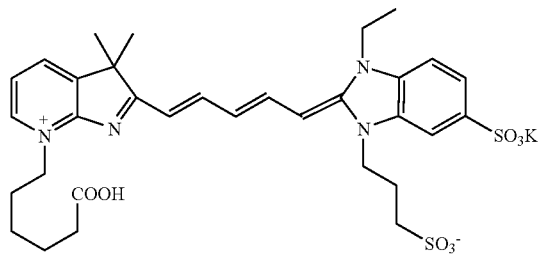
I-19
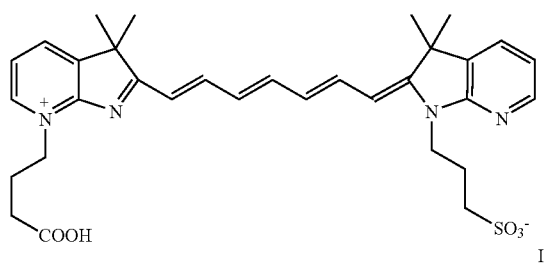
I-20
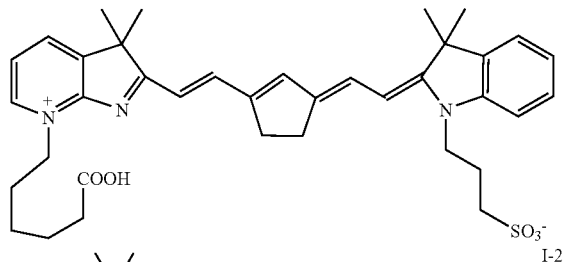
I-21
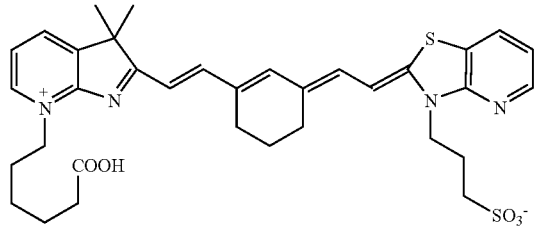
-continued
I-22
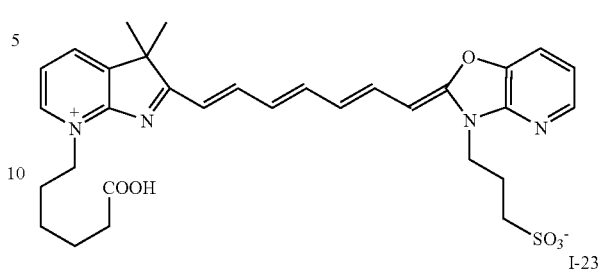
I-23
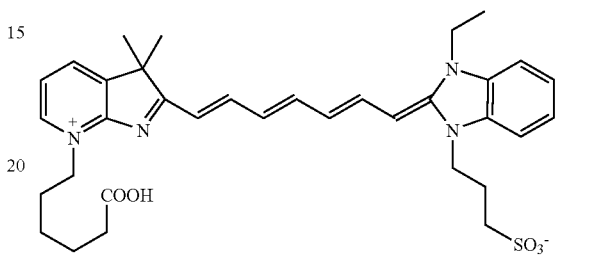
II-1
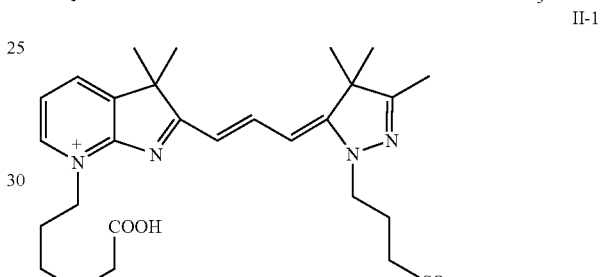
II-2
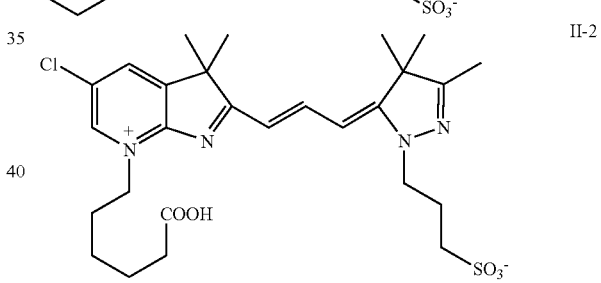
II-3
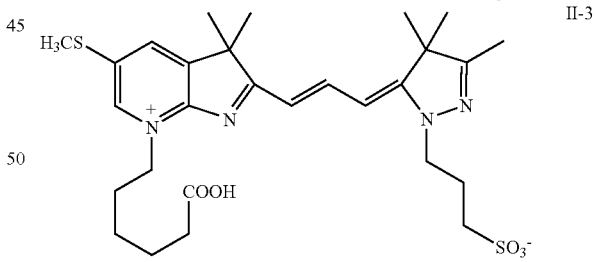
II-4
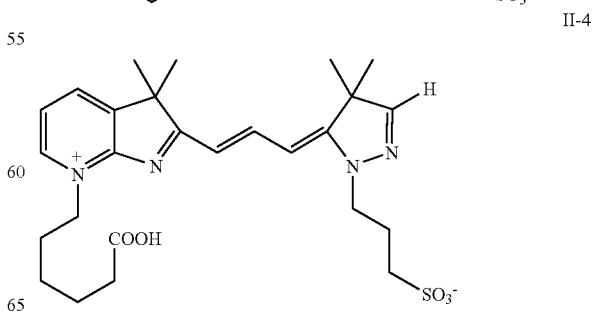

-continued
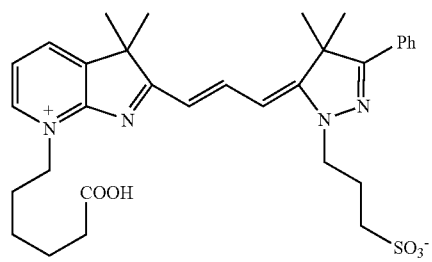
II-5
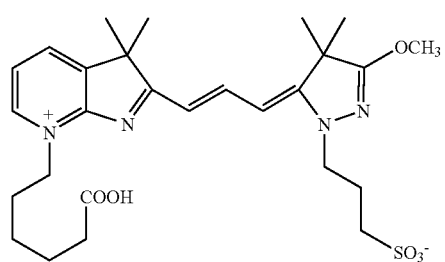
II-6
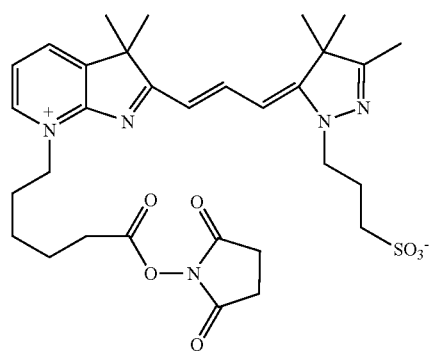
II-7
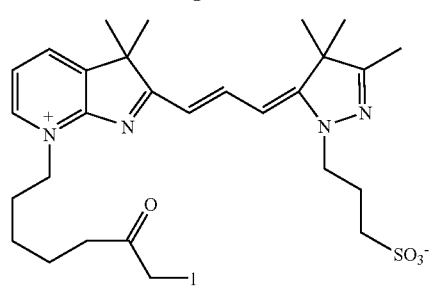
II-8
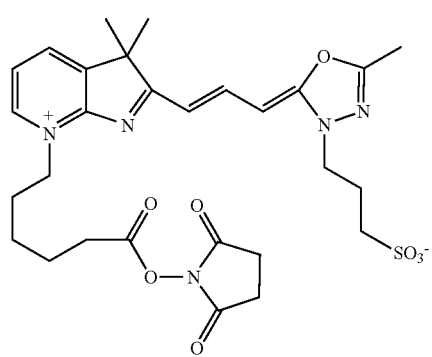
II-9
-continued
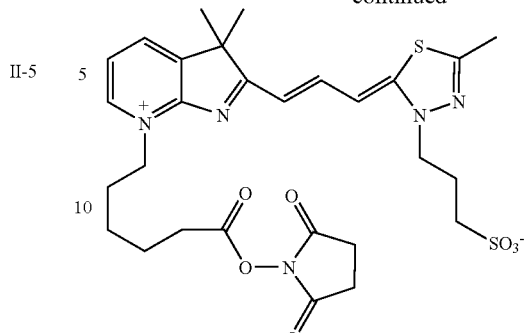
II-10
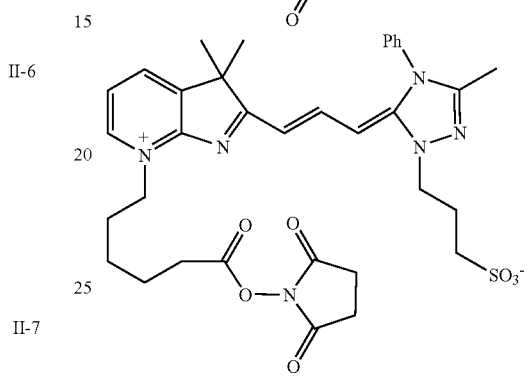
II-11
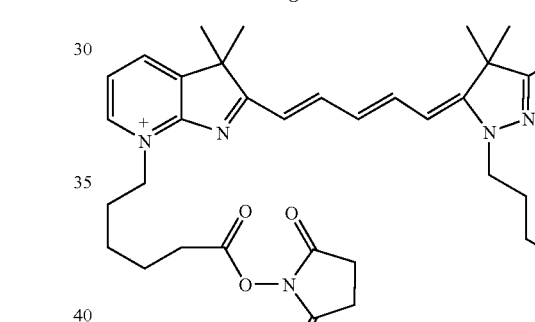
II-12
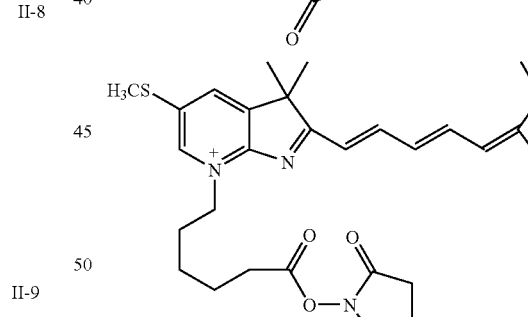
II-13
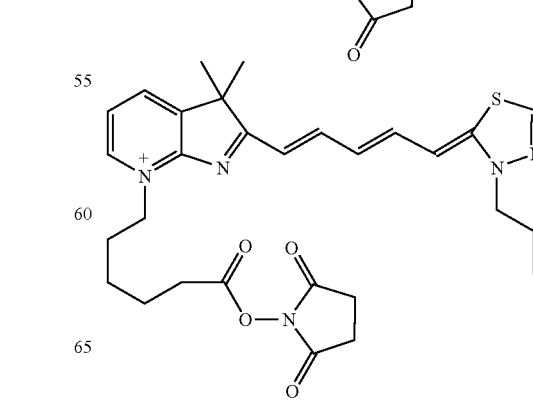
II-14

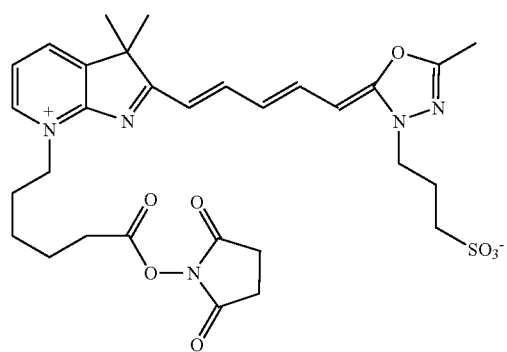
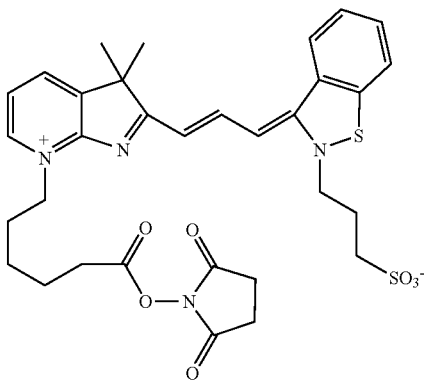
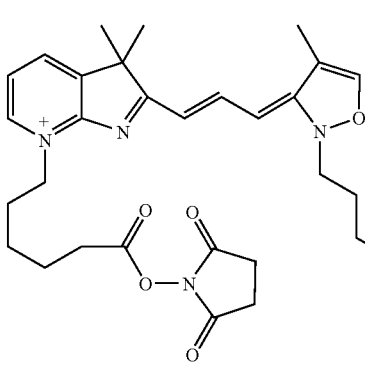
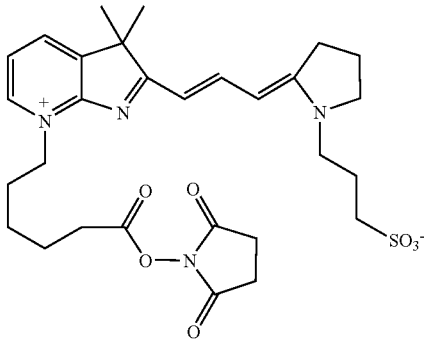
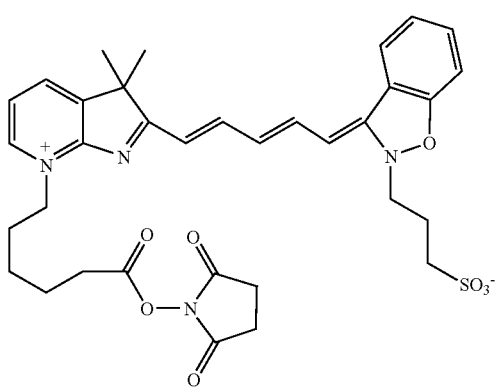

-continued

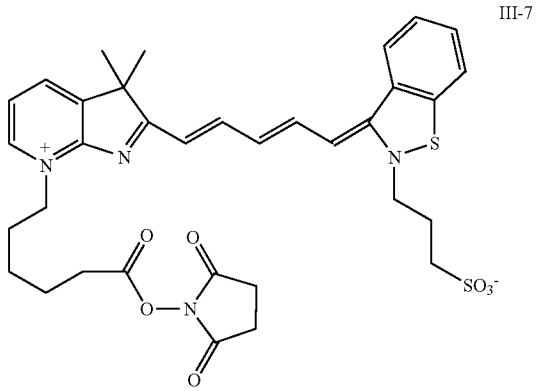

III-7

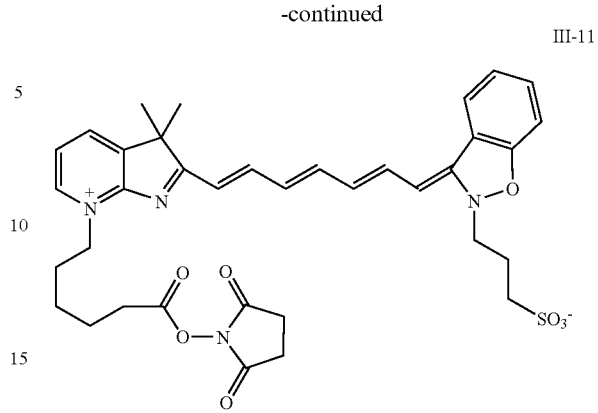

III-11

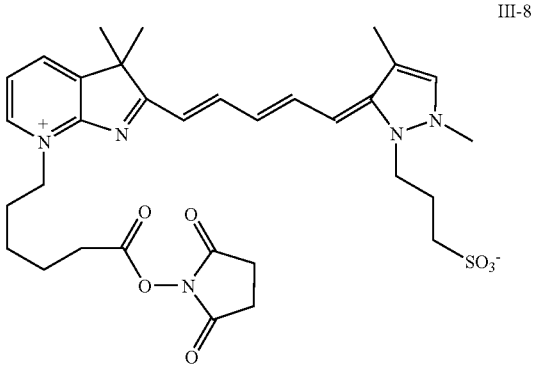

III-8

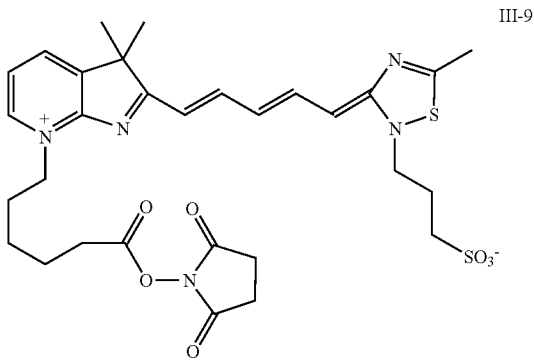

III-9

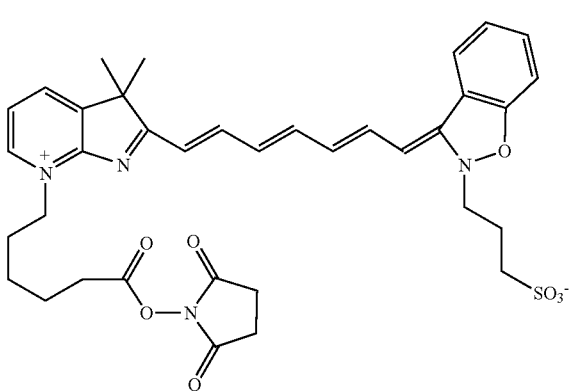

II-10

Methods for preparing typical compounds are specifically described in the examples of the specification. Accordingly, those skilled in the art can prepare any compound falling within the scope of any one of the aforementioned general formulas (I), (II), and (III) by suitably choosing a starting compound, reaction conditions, reagents and the like by referring to the specific explanations in the following examples, and by modifying or altering the methods described in the examples, as required. However, the methods for preparing the compounds represented by the aforementioned general formulas (I), (II), and (III) are not particularly limited, and those prepared by any methods can be used according to the present invention.

The compounds represented by the aforementioned general formulas (I), (II) and (III) are used as fluorescence-labeling components in the fluorescent nucleotides of the present invention. Various techniques for introducing nucleotides with the compounds represented by the general formulas (I), (II), and (III) as fluorescent labels are known, and those skilled in the art can suitably choose and use available means. For example, a functional group in a nucleotide such as an amino group and a hydroxyl group can be directly bind to a reactive substituent such as a carboxyl group and an active ester group in the compounds represented by the general formulas (I), (II), and (III) through an ionic bond or a covalent bond, or alternatively, a chemical modification into a part of a nucleotide such as introduction of a linker is applied, and then a resulting product is reacted with the compounds represented by the general formulas (I), (II), and (III). The fluorescent nucleotide produced after the reaction can be purified by commonly used separation techniques such as chromatography, electrophoresis, and recrystallization.

The present invention further relates to use of the fluorescent nucleotides of the present invention. That is, the fluorescent nucleotides of the present invention can be used to detect a nucleic acid. When the fluorescent nucleotides of the present invention are used for DNA analysis such as detection of a nucleic acid, the fluorescent nucleotides of the present invention can be incorporated into a probe or a primer, for example, according to the method described by Ruth (Jerry L. Ruth, DNA, 3, 123 (1984)). The present invention thus provides methods for preparing fluorescence-labeled nucleic acids which comprises the step of performing a nucleic acid synthesis reaction by using a nucleic acid synthetase, a template nucleic acid, and a fluorescent nucleotide of the present invention.

Examples of the nucleic acid synthetase used in the method of the present invention include DNA polymerase (including any DNA polymerase such as Klenow enzyme and Taq DNA polymerase), RNA polymerase, reverse transcriptase, terminal transferase and the like. However, the nucleic acid synthetase is not limited to these examples. Type of the template nucleic acid is not particularly limited and may be DNA or RNA. Naturally occurring DNA or RNA, as well as non-natural DNA or RNA such as recombinant DNA or RNA and chemically synthesized DNA or RNA may be used (the term "nucleic acid" referred to in the present specification has the same meanings). The nucleic acid synthesis reaction can be performed under conditions suitable for an enzymatic reaction (including conditions of salt concentration, pH, temperature and the like) by using, for example, template DNA, a non-fluorescent nucleotide mixture, a fluorescent nucleotide of the present invention, and nucleic acid synthetase. Such methods for synthesizing nucleic acids are known to those skilled in the art, and materials and reagents used can be suitably chosen by those skilled in the art depending on an object of labeling or the like.

Nucleic acids can be labeled by various methods using the fluorescent nucleotides of the present invention. The random prime method is one of methods for labeling DNA which includes a step of subjecting a mixture of hexanucleotide sequences in an arbitrary combination used as primer (random primer) to hybridize to a nucleic acid to be labeled. Starting from the 3'-OH end of this random primer, a strand complementary to a single strand is synthesized by using DNA polymerase such as Klenow enzyme or other DNA polymerase. At this time, four kinds of deoxyribonucleotides, which are the substrates of the DNA polymerase, are incorporated into the complementary strand. Complementary DNA labeled with the fluorescent nucleotide is synthesized by using the fluorescent nucleotide of the present invention as at least one kind of these deoxyribonucleotides.

Instead of the random primer, oligo DNA having a specific sequence (specific primer) can be used. The specific primer binds to a complementary region in the template DNA, and synthesis of DNA complementary to the template DNA is initiated from the 3'-OH end of the specific primer. As in the case of the random prime method, the fluorescent nucleotide of the present invention is incorporated when the complementary DNA is synthesized, and thus fluorescence-labeled complementary DNA is synthesized.

The nick translation method utilizes an action of DNase I on double-stranded DNA. A cleaved site is produced in a single strand of the template double-stranded DNA by the action of DNase I. *Escherichia coli* DNA polymerase I, four kinds of deoxyribonucleotides which are the substrates of this enzyme, and the fluorescent nucleotide of the present invention are added beforehand to a reaction mixture. The *Escherichia coli* DNA polymerase I cleaves a deoxyribonucleoside at the 5' end of the cleaved single strand, and simultaneously inserts one deoxyribonucleotide of the substrates at the position adjacent to the free 3'-OH end. By repeating this process, the cleaved site moves towards the 3' end. By adding the fluorescent nucleotide of the present invention into the nucleotides as the substrates, fluorescent DNA can be synthesized by the nick translation method.

In order to label the 3' end of double-stranded or single-stranded DNA, a terminal transferase can be used, which is an enzyme for adding a deoxyribonucleotide or ribonucleotide to the 3'-OH end. The terminal transferase requires at least one kind of deoxyribonucleotide or ribonucleotide as its substrate. By using the fluorescent nucleotide of the present invention as the substrate of the terminal transferase, a fluorescence-labeled nucleic acid extended at the 3'-OH end can be synthesized.

The reverse transcription reaction method utilizes a reaction of synthesizing complementary DNA from single-stranded RNA. First, as a primer, an oligo deoxyribonucleotide is annealed to a complementary region in RNA, and then an extension reaction is carried out by using a reverse transcriptase to synthesize a DNA strand complementary to the RNA strand initiating from the 3'-OH end of the primer. In this DNA synthesis, four kinds of deoxyribonucleotides are also used as the enzyme substrates, and when the fluorescent nucleotide of the present invention is added to the reaction system, the fluorescent nucleotide is inserted into the extended DNA strand during the reverse transcription reaction. Thus, fluorescence-labeled DNA is synthesized.

By using an enzyme synthesizing RNA from DNA, RNA labeled with the fluorescent nucleotide of the present invention can also be synthesized. Examples of the enzyme synthesizing RNA from DNA include RNA polymerases encoded by a phage such as SP6, T3 or T7 RNA polymerase. These enzymes are for synthesizing double-stranded DNA and RNA including an SP6, T3 or T7 promoter. As the substrates, four kinds of ribonucleotides are used. By using the fluorescent nucleotide of the present invention as one of the substrates, fluorescence-labeled RNA can be synthesized.

Nucleic acids labeled with the fluorescent nucleotide of the present invention can also be synthesized by performing polymerase chain reaction (PCR). In PCR, a nucleic acid to be detected in a biological sample is denatured into a single strand, and 2 kinds of primers are annealed to this single-stranded nucleic acid. After the annealing, an extension reaction is carried out by using a polymerase (preferably Taq DNA polymerase) and deoxyribonucleotides as the enzyme substrates. Starting from the 3'-OH end of the primer, complementary DNA can be synthesized to form double-stranded DNA. By repeating this process, DNA to be detected in the sample can be amplified. When the fluorescent nucleotide of the present invention is used as one of the substrates during the extension reaction using the Taq DNA polymerase, a fluorescence-labeled amplified nucleic acid can be obtained.

The fluorescent nucleic acids labeled with the fluorescent nucleotides of the present invention, which are prepared as described above, can be used as a gene probe for detecting a homologous nucleic acid sequence by hybridization. The fluorescent nucleotides hybridized with a target nucleic acid can be readily detected by measuring the fluorescence intensity using a fluorometer.

The fluorescent nucleotides of the present invention can be used to label gene probes, and the probes are useful as regents for detecting a nucleic acid, particularly diagnostic agents for diagnosing a disease of mammal including human. When probes labeled with the fluorescent nucleotides of the present invention are used as agents for detecting a nucleic acid or diagnostic agents, they can be supplied in the form of a agent composition by mixing one or more kinds of additives. For example, agents in a desired form of a solution or the like can be prepared by using suitable additives such as buffers, dissolving aids, pH modifiers, and preservatives. Those skilled in the art can suitably choose a form and a preparation method of the agents. The aforementioned diagnostic agents can be orally or parenterally administered to mammals including humans, or alternatively, by bringing a biological sample such as blood, urine, or saliva isolated or collected from a mammal including human into contact with the aforementioned diagnostic agents, diseases with abnormality of gene or the like can be diagnosed.

The fluorescent nucleotides of the present invention can be supplied in the form of a kit for detecting a nucleic acid together with an enzyme, a buffer and the like to be used in the aforementioned nucleic acid synthesis reaction. Kinds of reagents to be included in the kit can be suitably chosen depending on an object of the kit. In addition to the fluorescent nucleotide, nucleic acid synthetase and buffer, a mixture of one or more kinds (preferably four kinds) of non-fluorescent nucleotides, purified water and the like may be included in the kit as required. Primers such as random primers, oligo dT primers, specific primers for a particular purpose or the like may also be included in the kit.

EXAMPLES

The present invention will be explained more specifically with reference to the following examples. However, the scope of the present invention is not limited to these examples.

Synthetic Example 1

Synthesis of Compound I-1

Compound I-1 was synthesized by the synthetic route described below.

g, 10 mmol) and allowed to react at 100° C. for 2 hours. The reaction mixture was added with ethyl acetate (50 ml), and the resulting solid (2.8 g) was collected by filtration. The total volume of this solid was added with acetic anhydride (10 ml) and N,N'-diphenylformamidine (3.9 g, 20 mmol) and allowed to react at 100° C. for 30 minutes. After the reaction, the reaction mixture was added with ethyl acetate (50 ml) and hexane (50 ml), and the produced oil layer was separated by decantation. Compound I-1b (anil compound) was isolated by silica gel column chromatography.
Yield: 1.5 g (40%)
Mass (posi): 385

(Synthesis of Compound I-1a)

Compound I-1b (0.39 g, 1 mmol) and Compound I-1c (0.38 g, 1 mmol) were dissolved in DMF (5 ml), added with triethylamine (0.5 ml) and acetic anhydride (0.5 ml) and allowed to react at 60° C. for 1 hour. When the reaction mixture was added with ethyl acetate (50 ml), crystals were precipitated. The crude crystals were purified by gel filtration (Sephadex LH-20) to obtain Compound I-1a.

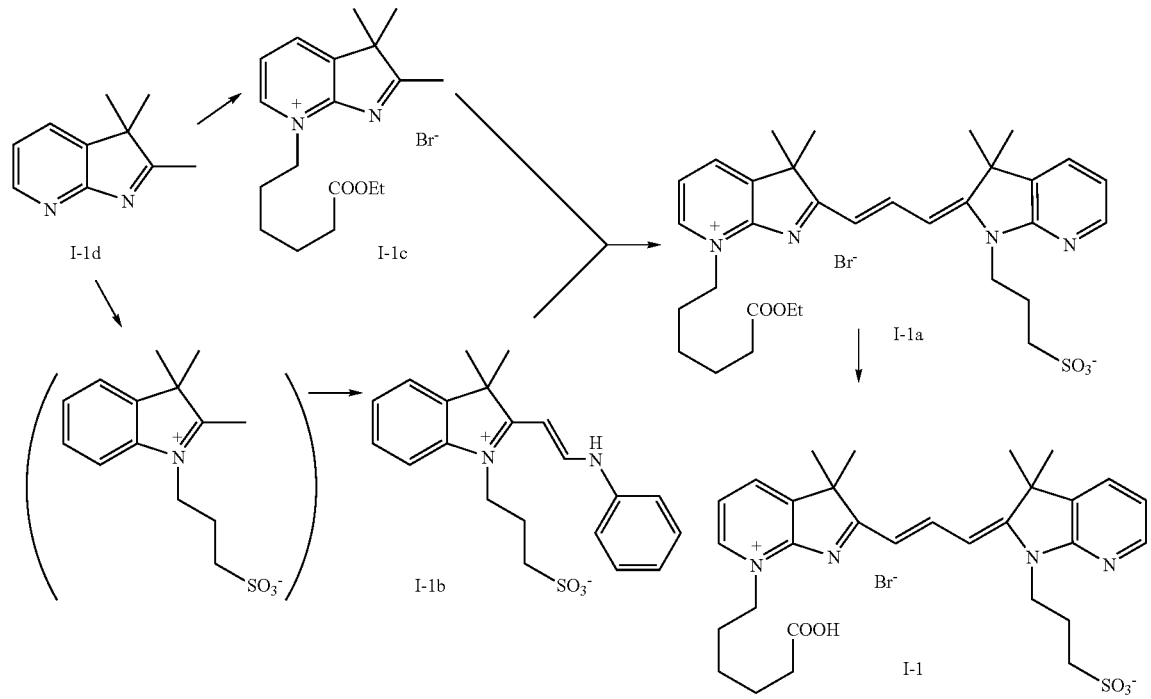

(Synthesis of Compound I-1c)

Compound I-1d (1.6 g, 10 mmol) was added with ethyl 6-bromohexanoate (2.4 g, 10.8 mmol) and allowed to react at 130° C. for 30 minutes. In this reaction, the nitrogen atom in the heterocyclic ring (indole ring moiety) other than the target site was also alkylated. However, by adding ethyl acetate (50 ml) and hexane (50 ml) to the reaction mixture after the reaction and separating the produced oil by decantation, only Compound I-1c was successfully separated, which was the objective product in which the nitrogen atom of the pyridine ring was quaternized.
Yield: 2.7 g (70%)
Mass (posi): 303

(Synthesis of Compound I-1b (anil compound))

Compound I-1d (1.6 g, 10 mmol) was dissolved in dimethylformamide (5 ml), added with propanesultone (1.2

Mass (posi): 594
Absorption maximum (methanol): 557 nm
Molar extinction coefficient: 81000

(Synthesis of Compound I-1)

The whole volume of Compound I-1a was dissolved in methanol (10 ml), added with 5% aqueous lithium hydroxide (5 ml) and allowed to react at room temperature for 2 hours. The reaction mixture was added with saturated aqueous sodium hydrogencarbonate (10 ml), and methanol was concentrated under reduced pressure to precipitate crude crystals of Compound I-1. The crude crystals were desalted by gel filtration (Sephadex LH-20) to obtain Compound I-1.
Yield: 0.20 g (35%, from I-1b)
Mass (posi): 566
Absorption maximum (methanol): 557 nm
Molar extinction coefficient: 82000

Synthetic Example 2

Syntheses of Compounds I-2 to I-5

Compounds I-2, I-3, I-4 and I-5 were synthesized according to the synthesis method of Compound I-1. Absorption characteristics of the compounds in methanol are shown in Table 1.

TABLE 1

| Compound No. | Absorption wavelength | Molar extinction coefficient |
|---|---|---|
| I-2 | 571 nm | 97000 |
| I-3 | 573 nm | 96000 |
| I-4 | 569 nm | 99000 |
| I-5 | 567 nm | 99000 |

Synthetic Example 4

Syntheses of Compounds I-10 to I-13

From the anil compounds derived from benzoxazole, indolenine, benzothiazole, and benzimidazole by a known method and Compounds I-1c, Compounds I-10 to I-13 were synthesized according to the synthetic methods of Compounds I-1a, I-1 and I-6. Since optimal conditions for synthesis of anil compound were different in the syntheses of Compounds I-10 to I-13, details of the conditions for anil syntheses are shown in Table 2. Absorption characteristics of Compounds I-10 to I-13 in methanol are shown in Table 3.

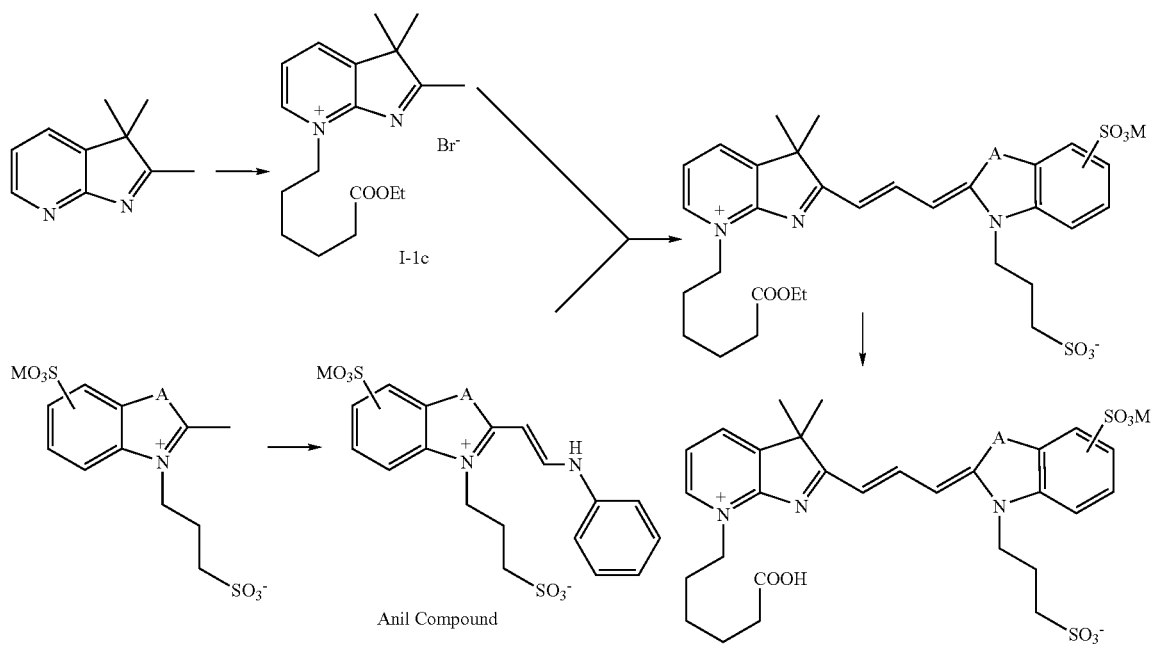

Synthetic Example 3

Synthesis of Compound I-6

Compound I-1 (0.57 g, 1 mmol) was dissolved in DMF (5 ml), added with pyridine (0.5 ml) and N,N'-disuccinimidyl carbonate (1.0 g) and allowed to react at 40° C. for 4 hours. The reaction mixture was added with ethyl acetate (50 ml), and the produced oil was separated by decantation. The oil was crystallized from diethyl ether to obtain Compound 1-6.

Yield: 0.5 g (74%)

Mass (posi): 663

Absorption maximum (methanol): 557 nm

Molar extinction coefficient: 88000

Compounds I-7 to I-9 were also synthesized from corresponding carboxylic acids according to the synthesis method of Compound I-6. The structure of each product was verified by mass spectrometry.

TABLE 2

| A in formula | Equivalent of N,N'-diphenylformamidine | Reaction temperature | Reaction time |
|---|---|---|---|
| O | 3 | 100° C. | 2 hours |
| C(Me)Me | 2 | 80° C. | 1 hour |
| S | 3 | 100° C. | 1 hour |
| N($C_2H_5$) | 5 | 170° C. | 6 hours |

TABLE 3

| Compound No. | Absorption wavelength | Molar extinction coefficient |
|---|---|---|
| I-10 | 549 nm | 120000 |
| I-11 | 561 nm | 105000 |
| I-13 | 558 nm | 125000 |
| I-14 | 548 nm | 105000 |

Synthetic Example 5

Synthesis of Compound I-14

Compound I-1d (1.6 g, 10 mmol) was dissolved in dimethylformamide (5 ml), added with propanesultone (1.2 g, 10 mmol) and allowed to react at 100° C. for 2 hours. The reaction mixture was added with ethyl acetate (50 ml), and the resulting solid (2.8 g) was collected by filtration. The whole volume of this solid was added with acetic anhydride (10 ml) and 3-anilino-acrylaldehydo-phenylimine (4.4 g, 20 mmol) and allowed to react at 100° C. for 30 minutes. The reaction mixture was added with ethyl acetate (50 ml), and the produced oil was separated by decantation. Subsequently, the oil was added with Compound I-1c (2.7 g, 7 mmol), dimethylformamide (10 ml), triethylamine (1 ml) and acetic anhydride (1 ml) and heated at 60° C. for 1 hour. The reaction mixture was added with ethyl acetate (50 ml), and the produced crude crystals were collected and purified by silica gel column chromatography to obtain ethyl ester of Compound I-14. Subsequently, the whole volume of the ethyl ester was subjected to ester hydrolysis under the conditions in the synthesis of Compound I-1 and purified by silica gel column chromatography to obtain Compound I-14.
Yield: 0.5 g (8%, from Compound I-d)
Mass (posi): 608
Absorption maximum (methanol): 639 nm
Molar extinction coefficient: 90000

Synthetic Example 6

Syntheses of Compounds I-15 to I-18

Compounds I-15 to I-18 were synthesized according to the method for producing Compound I-14. The dye structures were confirmed by mass spectrometry and absorption spectrometry.

Synthetic Example 7

Syntheses of Compounds I-19 to I-23

The title compounds were synthesized under the same conditions as the synthesis of Compound I-14 by using a glutaconaldehyde dianil derivatives instead of the 3-anilino-acrylaldehydo-phenylimine used in the synthesis of Compound I-14. In the synthesis of Compound I-22, decomposition of the dye was observed in the final step of ester hydrolysis, which resulted in a low yield.

Synthetic Example 8

Synthesis of Compound II-1

Compound II-1 was synthesized according to the following route.

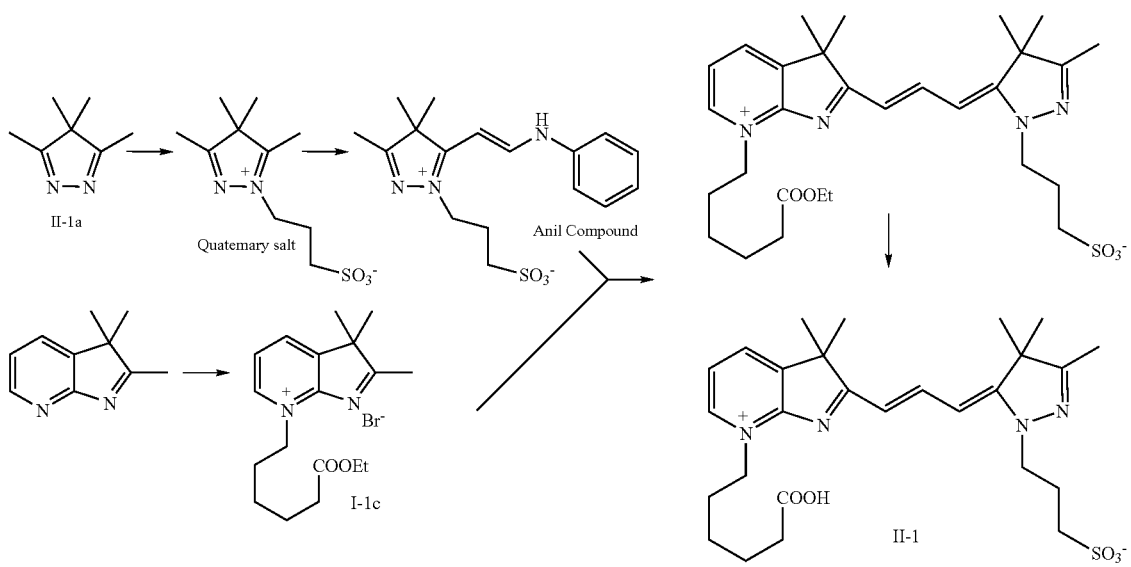

Compound II-1a (12.4 g, 0.1 mol) and propanesultone (12.2 g, 0.1 mol) were dissolved in toluene (30 ml) and refluxed with heating for 4 hours, and the quarternary salt precipitated in the reaction mixture was collected by filtration (quantitative). The whole amount of the product was added with acetonitrile (100 ml), N,N'-diphenylformamidine (19.6 g, 0.1 mol) and acetic anhydride (10.2 g, 0.1 mol), and refluxed with heating for 4 hours to obtain an anil compound (yield: 96%). The anil compound (0.35 g, 1 mmol) and Compound I-1c (0.38 g, 1 mmol) were dissolved in DMF (5 ml), added with triethylamine (0.5 ml) and acetic anhydride (0.5 ml) and allowed to react at 60° C. for 1 hour. When the reaction mixture was added with ethyl acetate (50 ml), crystals of ethyl ester were precipitated. The ethyl ester was recrystallized from a mixed solvent of chloroform and methanol. Then, the ester was hydrolyzed with methanol (10 ml) and 5% aqueous lithium hydroxide (5 ml) at room temperature for 2 hours and the resulting product was recrystallized from methanol to obtain Compound II-1.
Mass (posi): 530
Absorption maximum (methanol): 561 nm
Molar extinction coefficient: 125000

Synthetic Example 9

Syntheses of Compounds II-2 to II-17

Compounds II-2 to II-17 were synthesized according to the methods exemplified above. The dye structures were verified by mass spectrometry and absorption spectrometry. Absorption characteristics of these compounds in methanol are shown in Table 4.

TABLE 4

| Compound No. | Absorption wavelength | Molar extinction coefficient |
|---|---|---|
| II-2 | 570 nm | 135000 |
| II-3 | 561 nm | 125000 |
| II-4 | 558 nm | 120000 |
| II-5 | 587 nm | 145000 |
| II-6 | 561 nm | 133000 |
| II-7 | 561 nm | 120000 |
| II-8 | 561 nm | 125000 |
| II-9 | 522 nm | 120000 |
| II-10 | 562 nm | 131000 |
| II-11 | 525 nm | 110000 |
| II-12 | 660 nm | 200000 |
| II-13 | 660 nm | 200000 |
| II-14 | 661 nm | 210000 |
| II-15 | 640 nm | 195000 |
| II-16 | 750 nm | 240000 |

Synthetic Example 10

Synthesis of Compound III-1

Compound III-1 was obtained in the same manner as in the synthesis of Compound II-1 mentioned above under the same reaction conditions as the synthesis of Compound II-1, except that Compound II-1a as the starting material was replaced with 3-methyl-benzo[d]isoxazole.
Mass (posi): 636
Absorption maximum (methanol): 549 nm
Molar extinction coefficient: 145000

Synthetic Example 11

Synthesis of Compound III-3

According to the method described in Can. J. Chem., 66, 1405–1409 (1988), 3-methyl-benzo[d]isothiazole was synthesized, and Compound III-3 was synthesized in the same manner as in the synthesis of Compound III-1.
Mass (nega): 747
Absorption maximum (methanol): 555 nm
Molar extinction coefficient: 145000

Synthetic Example 12

Synthesis of Compound III-5

Compound III-5 was obtained in the same manner as in the synthesis of Compound II-1 mentioned above under the same reaction conditions as the synthesis of Compound II-1, except that Compound II-1a as the starting material was replaced with 2-methyl-1-pyrroline (Aldrich).
Mass (posi): 586
Absorption maximum (methanol): 520 nm
Molar extinction coefficient: 110000

(Comparison of Fluorescence Intensity)

The excitation wavelength and fluorescence intensity of the dyes of the present invention were compared with those of the conventional dyes shown below. Methanol was used as the solvent, and the dye concentration was set at $1.0 \times 10^{-6}$ M. Measurement was performed by using a spectrofluorophotometer RF-5300PC (Shimadzu Corporation). The results are shown in Tables 5 to 7. As shown in the tables, the dyes of the present invention showed high fluorescence intensity, and in particular, it can be understood that the dyes shown in Tables 5 and 6 have marked differences from the conventional dyes.

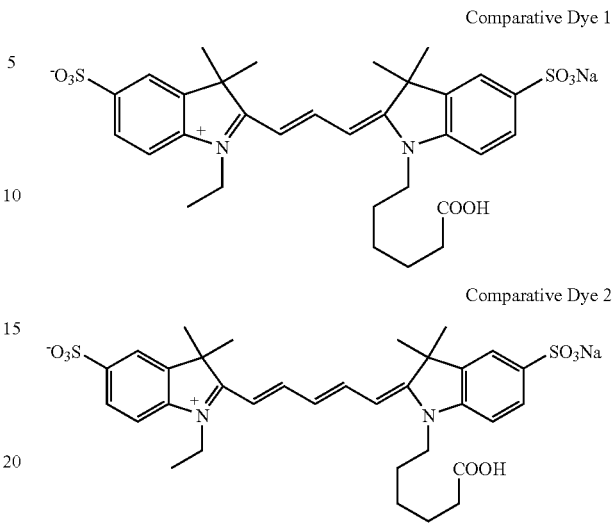

TABLE 5

| Compound No. | Excitation wavelength (nm) | Emission wavelength (nm) | Fluorescence intensity |
|---|---|---|---|
| Comparative Dye 1 | 555 | 568 | 20 |
| I-1 | 558 | 582 | 60 |
| I-2 | 571 | 592 | 110 |
| I-3 | 572 | 591 | 45 |
| I-4 | 561 | 585 | 100 |
| I-5 | 560 | 584 | 95 |
| I-6 | 558 | 582 | 52 |
| I-7 | 561 | 585 | 95 |
| I-8 | 560 | 584 | 95 |
| I-9 | 568 | 588 | 50 |
| I-10 | 549 | 563 | 120 |
| I-11 | 561 | 578 | 50 |
| I-12 | 561 | 578 | 35 |
| I-13 | 558 | 570 | 30 |

TABLE 6

| Compound No. | Excitation wavelength (nm) | Emission wavelength (nm) | Fluorescence intensity |
|---|---|---|---|
| Comparative Dye 1 | 555 | 568 | 13* |
| II-1 | 558 | 582 | 52 |
| II-2 | 571 | 592 | 70 |
| II-3 | 572 | 591 | 75 |
| II-4 | 561 | 585 | 27 |
| II-5 | 560 | 584 | 78 |
| II-6 | 558 | 582 | 37 |
| II-7 | 561 | 585 | 52 |
| II-8 | 560 | 584 | 49 |
| II-9 | 568 | 588 | 20 |
| II-10 | 549 | 564 | 52 |
| II-11 | 561 | 578 | 20 |
| III-1 | 549 | 562 | 100 |
| III-2 | 556 | 569 | 110 |
| III-3 | 568 | 575 | 45 |
| III-4 | 528 | 576 | 5 |
| III-5 | 519 | 536 | 17 |

*Deviated from the value of Table 5 due to change of xenon lamp

TABLE 7

| Compound No. | Excitation wavelength (nm) | Emission wavelength (nm) | Fluorescence intensity |
|---|---|---|---|
| Comparative dye 2 | 647 | 666 | 80 |
| I-14 | 639 | 677 | 88 |
| I-15 | 644 | 661 | 150 |
| I-16 | 650 | 671 | 81 |
| I-17 | 643 | 677 | 95 |
| I-18 | 645 | 667 | 78 |
| II-12 | 658 | 676 | 90 |
| II-13 | 661 | 678 | 95 |
| II-14 | 659 | 675 | 95 |
| II-15 | 645 | 662 | 75 |
| III-6 | 645 | 662 | 100 |
| III-7 | 658 | 678 | 80 |
| III-8 | 654 | 673 | 78 |
| III-9 | 658 | 675 | 75 |

Example 1

Synthesis of Compound I-1-dUTP conjugate

Compound I-1 (5 mg, 2.5 parts) was dissolved in 0.1 M MES buffer (2 ml), added with WSC hydrochloride (3.66 mg, 5 parts) and Sulfo-NHS (4.20 mg, 5 parts) and stirred at room temperature for 15 minutes. The reaction mixture was added with aminoallyl-dUTP (2.2 mg, Sigma) dissolved in 0.1 M MES (200 µl) and allowed to react at room temperature for 2 hours. The reaction mixture was added with 1 M Tris buffer (100 µl, pH 7.5) to terminate the reaction, adsorbed on a column filled with 8 g of ODS silica (YMC-ODS-AQ 120A) and eluted with 30% aqueous methanol solution. The eluate was concentrated and further purified by medium pressure preparative chromatography (YAMAZEN Ultrapack ODS-S-40B) to obtain the target substance with purity of 95% (yield: 71%).

MS analytical value: M-1072

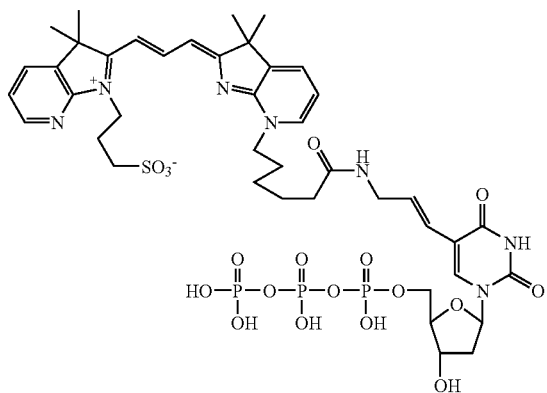

Example 2

Synthesis of Compound I-14-dUTP conjugate

Compound I-14 (5.5 mg, 2.5 parts) was dissolved in DMSO (200 µl), added with WSC hydrochloride (3.1 mg, 5 parts) and Sulfo-NHS (3.55 mg, 5 parts) and stirred at room temperature for 15 minutes. The reaction mixture was added with aminoallyl-dUTP (2.2 mg, Sigma) dissolved in 0.1 M MES (2 ml) and allowed to react at room temperature for 2 hours. The reaction mixture was added with 1 M Tris buffer (100 µl pH 7.5) to terminate the reaction, adsorbed on a column filled with 8 g of ODS silica (YMC-ODS-AQ 120A) and eluted with 45% aqueous methanol solution. The eluate was concentrated and further purified by medium pressure preparative chromatography (YAMAZEN Ultrapack ODS-S-40B) to obtain the target substance with purity of 94% (yield: 68%).

MS analytical value: M-1098

Example 3

Synthesis of Compound II-1-dUTP Conjugate

Compound II-1 (6.00 mg, 2.5 parts) was dissolved in DMSO (200 µl), added with WSC hydrochloride (3.1 mg, 5 parts) and Sulfo-NHS (3.55 mg, 5 parts) and stirred at room temperature for 30 minutes. The reaction mixture was added with aminoallyl-dUTP (2.2 mg, Sigma) dissolved in 0.1 M MES (2 ml) and allowed to react at room temperature for 2 hours. The mixture was added with 1 M Tris buffer (100 µl, pH 7.5) to terminate the reaction, adsorbed on a column filled with 8 g of ODS silica (YMC-ODS-AQ 120A) and eluted with 50% aqueous methanol solution. The eluate was concentrated and further purified by medium pressure preparative chromatography (YAMAZEN Ultrapack ODS-S-40B) to obtain the target substance with purity of 92% (yield: 74%).

MS analytical value: M-1036

Example 4

Synthesis of Compound II-12-dUTP Conjugate

Compound II-12 (3.27 mg, 1.0 part) was dissolved in DMSO (200 µl), added with aminoallyl-dUTP (2.2 mg, Sigma) dissolved in 0.1 M MES (2 ml) and allowed to react at room temperature for 2 hours. The reaction mixture was added with 1 M Tris buffer (100 µl, pH 7.5) to terminate the reaction, adsorbed on a column filled with 8 g of ODS silica (YMC-ODS-AQ 120A) and eluted with 40% aqueous methanol solution. The eluate was concentrated and further purified by medium pressure preparative chromatography (YAMAZEN Ultrapack ODS-S-40B) to obtain the target substance with purity of 95% (yield: 77%).

MS analytical value: M-1062

Example 5

Synthesis of Compound III-1-dUTP Conjugate

Compound III-1 (1.00 mg, 1.0 part) was dissolved in 0.1 M MES (300 µl), added with aminoallyl-dUTP (0.25 mg, 0.4 part, Sigma), further added with 1 M carbonate buffer (300 µl, pH 9.0) and allowed to react overnight at room temperature. The mixture was added with 1 M Tris buffer (100 µl, pH 7.5) to terminate the reaction and purified by medium pressure preparative chromatography (YAMAZEN Ultrapack ODS-S-40B) to obtain the target substance with purity of 90% (yield: 62%).

MS analytical value: M-1044

Example 6

Synthesis of Compound III-7-dUTP Conjugate

Compound III-7 (1.00 mg, 1.0 part) was dissolved in 0.1 M MES (300 µl), added with aminoallyl-dUTP (0.66 mg, 1.0 part, Sigma), further added with 0.1 M carbonate buffer (300 µl, pH 9.0) and allowed to react overnight at room temperature. The reaction mixture was added with 0.1 M Tris buffer (100 µl, pH 7.5) to terminate the reaction and purified by medium pressure preparative chromatography (YAMAZEN Ultrapack ODS-S-40B) to obtain the target substance with purity of 96% (yield: 44%).
MS analytical value: M-1070

Application Example 1

Preparation of Fluorescence-labeled DNA Probe Utilizing Transcription Reaction

Human liver mRNA (0.5 μg, Clontech) and oligo dT primer (0.5 μg, dT18-21, Gibco BRL) were mixed, heated at 70° C. for 10 minutes and rapidly cooled on ice. This mixture was added with RnaseOUT (40 U, Gibco BRL), dATP (500 μM), dGTP (500 μM), dCTP (500 μM), dTTP (200 μM), the Compound I-1-dUTP conjugate (100 μM) obtained in Example 1, SuperScript II reverse transcriptase (400 U, Gibco BRL) and DEPC-treated water (in an amount required to make 20 μl of the total volume) and allowed to react at 42° C. for 2 hours. After the completion of the reaction, the reaction mixture was added with EDTA and NaOH and incubated at 65° C. for 1 hour to terminate the reaction and decompose mRNA. The reaction mixture was passed through a CentriSep column (Princeton Separation, Inc.) to remove unreacted Compound I-1-dUTP conjugate and the like for purification.

For comparison, a reverse transcription reaction was performed in the same manner as described above by using a comparative fluorescent nucleotide labeled with a dye (Cy3) (Cy3-AP3-dUTP, Amersham Pharmacia Biotech) instead of the Compound I-1-dUTP conjugate, and the reaction product was purified. After the purification, each reaction mixture was subjected to agarose gel electrophoresis, stained with SYBR Green II (Molecular Probes) and scanned by FLA2000 (Fuji Photo Film Co., Ltd.). As a result, it was found that the fluorescence intensity was higher and was detectable more clearly when the Compound I-1-dUTP conjugate of the present invention was used. Further, the fluorescence intensity was measured by a fluorometer, and the DNA amount was measured based on absorption at 260 nm. From these results, uptake rate and fluorescence intensity per 1 μM of probe were calculated. The results are shown in Table 8. As shown by the results in Table 8, the uptake rate and the fluorescence intensity became higher when the Compound I-1-dUTP conjugate of the present invention was used.

TABLE 8

| Fluorescent compound | Uptake rate (Dye/1 kb) | Fluorescence intensity |
|---|---|---|
| Compound I-1-dUTP conjugate | 15 | 2000 |
| Cy3-AP3-dUTP for comparison | 12 | 700 |

Application Example 2

Preparation of DNA Probe Labeled with Fluorescent Dye by PCR Composition of PCR reaction mixture:
Template DNA: 10 pg
Primers 1 and 2: 0.5 μM each
dATP, dGTP, dCTP: 200 μM each
dTTP: 150 μM
Compound II-1-dUTP conjugate or Cy3-AP3-dUTP: 50 μM
Pyrobest DNA polymerase (TAKARA): 0.5 unit
Sterilized water: amount to make 20 μl of total volume
(Note: as the template DNA, PCR-Script™ SK(+) (Stratagene) incorporated with α-2-HS-glycoprotein gene was used, and the sequences of Primers 1 and 2 are shown as SEQ ID NOS: 1 and 2 in Sequence Listing, respectively.)

PCR was performed by using a solution having the above composition as the PCR reaction mixture and repeating a cycle of reactions at 94° C. for 30 seconds, 60° C. for 30 seconds and 72° C. for 30 seconds for 30 cycles. The reaction mixture was passed through a CentriSep column (Princeton Separation, Inc.) to remove unreacted fluorescent nucleotides and the like for purification of the product. After the purification, the reaction mixture was subjected to agarose gel electrophoresis, stained with SYBR Green II (Molecular Probes) and scanned by FLA2000 (Fuji Photo Film Co., Ltd.). As a result, it was found that the fluorescence intensity became higher and was detectable more clearly when the Compound II-1-dUTP conjugate of the present invention was used. Further, the fluorescence intensity was measured by a fluorometer and the DNA amount was measured based on absorption at 260 nm. From these results, uptake rate and fluorescence intensity per 1 μM of probe were calculated. The results are shown in Table 9. As shown by the results in Table 9, the uptake rate and the fluorescence intensity became higher when the Compound II-1-dUTP conjugate of the present invention was used.

TABLE 9

| Fluorescent compound | Uptake rate (Dye/1 kb) | Fluorescence intensity |
|---|---|---|
| Compound II-1-dUTP conjugate | 18 | 2500 |
| Cy3-AP3-dUTP for comparison | 12 | 700 |

The fluorescent nucleotides of the present invention have superior uptake rate upon DNA synthesis and fluorescence intensity after the uptake, and thus they are useful as substances for labeling nucleic acids.

What is claimed is:

1. A fluorescent nucleotide represented by the formula: X—Y—Z wherein,

X represents a residue of a natural or non-natural nucleotide, an oligonucleotide, or a polynucleotide, which binds to Y at a basic moiety of said residue;

Y represents a divalent bridging group or a single bond; and

Z represents a monovalent group derived from:

a compound represented by the following general formula (II):

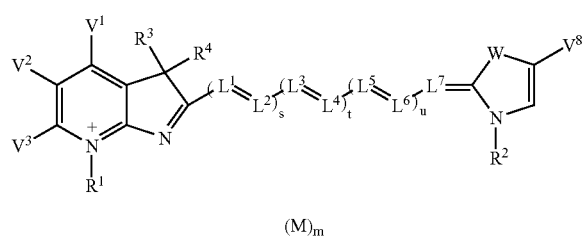

(M)$_m$ wherein, $R^1$, $R^2$, $R^3$, and $R^4$ each independently represents a substituted or unsubstituted alkyl group, and $R^3$ and $R^4$ may bind to each other to form a saturated or unsaturated ring; $V^1$, $V^2$ and $V^3$ each independently represents a hydrogen atom or a substituent, $V^1$ and $V^2$, and/or $V^2$ and $V^3$ may bind to each other to form a saturated or unsaturated ring; $L^1$, $L^2$, $L^3$, $L^4$, $L^5$, $L^6$ and $L^7$ each independently represents a substituted or unsubstituted methine group; W represents an oxygen atom, a sulfur atom, —C($R^3$)($R^4$)— or —N($R^5$)— wherein $R^3$, $R^4$, and $R^5$ each independently represents a substituted or unsubstituted alkyl group; Q represents a nitrogen atom or C($V^7$) wherein $V^7$ represents a hydrogen atom or a monovalent substituent and may bind to $V^6$ to form a saturated or unsaturated ring; M represents a counter ion; m represents a number required to neutralize the charge of the molecule; s represents 0 or 1; t represents 0 or 1; and u represents 0 or 1; and $V^8$ represents a hydrogen atom or a malevolent substituent, provided that, when W represents —N($R^5$)— or —C($R^3$)($R^4$)—, $V^8$ may bind to a substituent on W to form a saturated or unsaturated ring; or a compound represented by the following general formula (III):

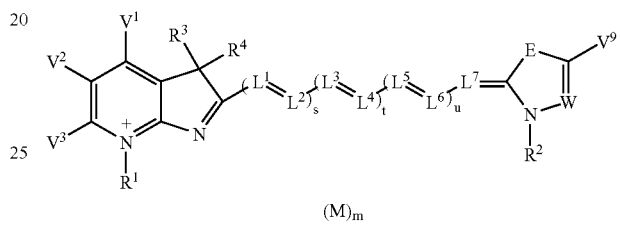

(M)$_m$ wherein, $V^1$, $V^2$, $V^3$, $R^1$, $R^2$, $R^3$, $R^4$, $L^1$, $L^2$, $L^3$, $L^4$, $L^5$, $L^6$, $L^7$, W, M, m, s, t, and u have the same meanings as defined above; E represents a nitrogen atom or —C($R^6$)=, where $R^6$ represents a hydrogen atom or a monovalent substituent; $V^9$ represents a hydrogen atom or a monovalent substituent and $V^9$ may bind to $R^6$ to form a saturated or unsaturated ring, and Z binds to Y at a reactive group existing in $R^1$ or $R^2$.

2. The fluorescent nucleotide according to claim 1, wherein at least one of $R^1$ and $R^2$ is an alkyl group substituted with an active ester group in Y, wherein said active ester group can covalently bond to an amino group, a hydroxyl group, or a thiol group.

3. The fluorescent nucleotide according to claim 1, wherein at least one of $R^1$ and $R^2$ is an alkyl group substituted with a carboxyl group in Y.

4. The fluorescent nucleotide according to claim 1, wherein X is a residue of a natural or non-natural nucleotide.

5. The fluorescent nucleotide according to claim 1, wherein X is selected from the group consisting of: AMP, ADP, ATP, GMP, GDP, GTP, CMP, CDP, CTP, UMP, UDP, UTP, TMP, TDP, TTP, 2-Me-AMP, 2-Me-ADP, 2-Me-ATP, 1-Me-GMP, 1-Me-GDP, 1-Me-GTP, 5-Me-CMP, 5-Me-CDP, 5-Me-CTP, 5-MeO-CMP, 5-MeO-CDP, and 5-MeO-CTP, wherein Me represents a methyl group, MeO represents a methoxy group, and a numeral before Me or MeO represents a substituting position, and wherein X may be a corresponding deoxynucleotide or dideoxynucleotide.

6. The fluorescent nucleotide according to claim 1, wherein Y represents —CH$_2$—, —CH=CH—, —C≡C—, —CO—, —O—, —S—, —NH—, or a bridging group consisting of a combination thereof wherein a hydrogen atom on the bridging group may be replaced with other substituent.

7. The fluorescent nucleotide according to claim 1, wherein Y represents an aminoalkyl group.

8. A method for producing a fluorescence-labeled nucleic acid which comprises a step of performing a nucleic acid synthesis reaction by using a nucleic acid synthetase, a template nucleic acid, and the fluorescent nucleotide according to claim 1.

9. The method according to claim 8, wherein the nucleic acid synthesis reaction comprises one or more reactions selected from the group consisting of a reverse transcription reaction, terminal transferase reaction, reactions of random prime method, PCR, and nick translation.

10. A nucleic acid probe or a primer labeled with the fluorescent nucleotide according to claim 1.

11. An agent for detecting a nucleic acid which comprises the nucleic acid probe or the primer according to claim 10.

12. The agent according to claim 11, wherein said nucleic acid is indicative of a disease.

13. A kit for detecting a nucleic acid, which comprises:
   (1) the fluorescent nucleotide according to claim 1;
   (2) a nucleic acid synthetase; and
   (3) a buffer.

14. An azamethine dye represented by the following general formula (II):

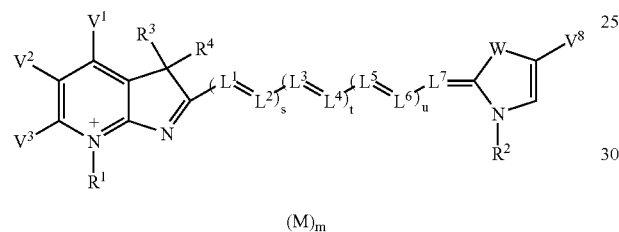

$(M)_m$ wherein $R^1$, $R^2$, $R^3$, and $R^4$ each independently represents a substituted or unsubstituted alkyl group, and $R^3$ and $R^4$ may bind to each other to form a saturated or unsaturated ring; $V^1$, $V^2$ and $V^3$ each independently represents a hydrogen atom or a substituent, $V^1$ and $V^2$, and/or $V^2$ and $V^3$ may bind to each other to form a saturated or unsaturated ring; $V^8$ represents a hydrogen atom or a monovalent substituent; $L^1$, $L^2$, $L^3$, $L^4$, $L^5$, $L^6$ and $L^7$ each independently represents a substituted or unsubstituted methine group; W represents an oxygen atom, a sulfur atom, $-C(R^3)(R^4)-$ or $-N(R^5)-$ wherein $R^3$, $R^4$, and $R^5$ each independently represents a substituted or unsubstituted alkyl group, provided that, when W represents $-N(R^5)-$ or $-C(R^3)(R^4)-$, $V^8$ may bind to a substituent on W to form a saturated or unsaturated ring; M represents a counter ion; m represents a number required to neutralize the charge of the molecule; s represents 0 or 1; t represents 0 or 1; and u represents 0 or 1.

15. An azamethine dye represented by the following general formula (III):

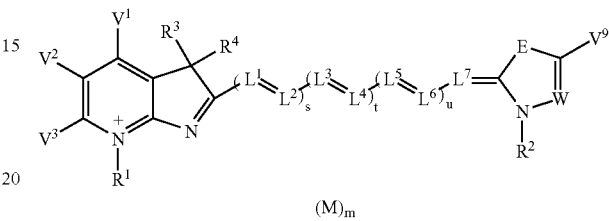

$(M)_m$ wherein $R^1$, $R^2$, $R^3$, and $R^4$ each independently represents a substituted or unsubstituted alkyl group, $R^3$ and $R^4$ may bind to each other to form a saturated or unsaturated ring; $V^1$, $V^2$, $V^3$ each independently represents a hydrogen atom or a substituent, $V^9$ represents hydrogen or a monovalent substituent, $V^1$ and $V^2$, and/or $V^2$ and $V^3$ may bind to each other to form a saturated or unsaturated ring; $L^1$, $L^2$, $L^3$, $L^4$, $L^5$, $L^6$ and $L^7$ each independently represents a substituted or unsubstituted methine group; W represents an oxygen atom, a sulfur atom, $-C(R^3)(R^4)-$ or $-N(R^5)-$ wherein $R^3$, $R^4$, and $R^5$ each independently represents a substituted or unsubstituted alkyl group; E represents a nitrogen atom or $-C(R^6)=$, where $R^6$ represents a hydrogen atom or a monovalent substituent, and $V^9$ may bind to form a saturated or unsaturated ring; M represents a counter ion; m represents a number required to neutralize the charge of the molecule; s represents 0 or 1; t represents 0 or 1; and u represents 0 or 1.

* * * * *